US006873916B2

(12) United States Patent
Kolosov et al.

(10) Patent No.: US 6,873,916 B2
(45) Date of Patent: Mar. 29, 2005

(54) APPLICATION SPECIFIC INTEGRATED CIRCUITRY FOR CONTROLLING ANALYSIS OF A FLUID

(75) Inventors: Oleg V. Kolosov, San Jose, CA (US); Leonid Matsiev, San Jose, CA (US); Mikhail B. Spitkovsky, Sunnyvale, CA (US); Vladimir Gammer, San Francisco, CA (US)

(73) Assignee: Symyx Technologies, Inc., Santa Clara, CA (US)

( * ) Notice: Subject to any disclaimer, the term of this patent is extended or adjusted under 35 U.S.C. 154(b) by 3 days.

(21) Appl. No.: 10/394,543

(22) Filed: Mar. 21, 2003

(65) Prior Publication Data

US 2004/0107055 A1 Jun. 3, 2004

Related U.S. Application Data

(60) Provisional application No. 60/419,404, filed on Oct. 18, 2002.

(51) Int. Cl.[7] .................................... G01N 31/00
(52) U.S. Cl. .................................... 702/25
(58) Field of Search .................... 702/25, 45, 50, 702/54, 56, 100, 104, 106; 73/53.01, 54.24, 54.41

(56) References Cited

U.S. PATENT DOCUMENTS

| | | | |
|---|---|---|---|
| 4,429,564 A | 2/1984 | Ikeda et al. | 73/32 |
| 4,893,496 A | 1/1990 | Bau et al. | 73/32 A |
| 5,181,423 A | 1/1993 | Philipps et al. | 73/724 |
| 5,524,477 A | 6/1996 | Wajid | 73/24.05 |
| 5,528,924 A | 6/1996 | Wajid et al. | 73/24.06 |
| 5,741,961 A | 4/1998 | Martin et al. | 73/32 R |
| 5,780,191 A | 7/1998 | Ide | 430/45 |
| 5,886,250 A | 3/1999 | Greenwood et al. | 73/32 A |
| 5,921,928 A | 7/1999 | Greenleaf et al. | 600/437 |

(Continued)

FOREIGN PATENT DOCUMENTS

| | | | |
|---|---|---|---|
| DE | 44 24 422 A1 | 7/1994 | 29/2 |
| DE | 100 14 724 A1 | 3/2000 | 23/28 |
| EP | 58003238 | 1/1983 | 11/16 |
| EP | 0 282 251 A2 | 9/1988 | G01N/9/00 |
| EP | 96307419.0 | 10/1996 | 29/2 |
| EP | 88301957.2 | 3/1998 | |
| GB | 2 369 887 A | 6/2002 | G01N/9/00 |
| JP | 06271690 | 9/1994 | 45/2 |

OTHER PUBLICATIONS

William H. et al., "*Downhill Simplex Method in Multidimensions*", pp. 305–309, Numerical Recipes in C: The Art of Scientific Computing, Cambridge University Press, 1988.

Hammond et al., "*An Acoustic Automotive Engine Oil Quality Sensor*", 1997 IEEE Int'l Frequency Control Symp., pp. 72–80, Dept. of Elec. & Computer Eng., University of Maine.

(Continued)

*Primary Examiner*—Michael Nghiem
(74) *Attorney, Agent, or Firm*—Martine & Penilla, LLP

(57) ABSTRACT

A circuit for determining characteristics of a fluid under-test is provided. The circuit includes analog-to-digital processing circuitry for interfacing with a sensor and host electronics. The analog-to-digital processing circuitry includes a frequency generator for providing stimulus to the sensor and receiving a response signal from the sensor. Conditioning circuitry for reducing analog signal offsets in the response signal and signal detection circuitry for identifying amplitude data of the response signal are provided. Further provided is analog-to-digital conversion circuitry for converting the detected amplitude data into digital form. Memory for holding calibration data and approximated fluid characteristics of the fluid under-test is included in the circuitry. The digital form of the response signal is processed in conjunction with the calibration data and approximated fluid characteristics to generate fluid characteristics of the actual fluid under-test.

52 Claims, 16 Drawing Sheets

U.S. PATENT DOCUMENTS

| | | | | | |
|---|---|---|---|---|---|
| 6,044,694 | A | | 4/2000 | Anderson et al. | 73/54.41 |
| 6,082,180 | A | | 7/2000 | Greenwood | 73/32 A |
| 6,082,181 | A | | 7/2000 | Greenwood | 73/32 A |
| 6,182,499 | B1 | * | 2/2001 | McFarland et al. | 73/24.06 |
| 6,223,589 | B1 | | 5/2001 | Dickert et al. | 73/61.45 |
| 6,269,686 | B1 | | 8/2001 | Hahn et al. | 73/54.24 |
| 6,311,549 | B1 | | 11/2001 | Thundat et al. | 73/54.24 |
| 6,336,353 | B2 | | 1/2002 | Matsiev et al. | 73/24.06 |
| 6,378,364 | B1 | | 4/2002 | Pelletier et al. | 73/152.47 |
| 6,389,891 | B1 | | 5/2002 | D'Angelico et al. | 73/290 V |
| 6,393,895 | B1 | | 5/2002 | Matsiev et al. | 73/24.06 |
| 6,401,519 | B1 | | 6/2002 | McFarland et al. | 73/24.06 |
| 6,494,079 | B1 | | 12/2002 | Matsiev et al. | 73/24.05 |
| 6,714,604 | B1 | * | 3/2004 | Tsurumi et al. | 375/329 |
| 2003/0041653 | A1 | * | 3/2003 | Matsiev et al. | 73/54.25 |

OTHER PUBLICATIONS

Schweyer et al., "*A Novel Monolithic Piezoelectric Sensor*", 1997 IEEE Int'l Frequency Control Symp., pp. 32–40, Dept. of Elec. & Computer Eng., University of Maine.

Dring, A. et al., "*Integrated on–line multisensing of fluid flow using a mechanical resonator*", 2000, Sensors and Actuators 85, pp. 275–279, The Brunel Centre for Manufacturing Metrology, Brunel University, Uxbridge, Middlesex, UB8 3PH, UK.

Shih, W. et al., "*Simutaneous liquid viscosity and density determination with piezoelectric unimorph cantilevers*", 2001, Journal of Applied Physics, vol. 89, No. 2, pp. 1497–1505, 2001 American Institute of Physics: XP–001011783.

Sorab, J. et al., "*Engine Oil Viscosity Sensors Using Disks of PZT Ceramic as Electromechanical Vibrators*", 1997, International Spring Fuels & Lubricants Meeting, Understanding Engine Oil Rheology and Tribology (SP–1271), pp. 85–91, SAE Technical Paper Series; 971702, SAE The Engineering Society For Advancing Mobility Land Sea Air and Space International.

Zhang, J. et al., "*Determination of liquid density with a low frequency mechanical sensor based on quartz tuning fork*", 2002, Sensors and Actuators B 84, pp. 123–128, Micro and . . . Institute of Material Research and Engineering, Research Link 3, Singapore.

International Search Report, Oct. 6, 2004, pp. 2, 5.*

* cited by examiner

COMPUTER
123
DIGITAL PROCESSOR
138
ECU
121
120

ASIC
118
(TF) SENSOR
116
122
USER INTERFACE
DIGITAL DISPLAY
122c
USER INPUT
122a
122b
122d

FIG. 2D

| TUNING FORK 1.1 TEMP. 25° C | APPROXIMATED FLUID CHARACTERISTICS | DENSITY | VISCOSITY | DIELECTRIC CONSTANT |
|---|---|---|---|---|
| | OIL TYPE 1 | $\rho$ | $\eta$ | $\varepsilon$ |
| | OIL TYPE 2 | $\rho$ | $\eta$ | $\varepsilon$ |
| | OIL TYPE 3 | $\rho$ | $\eta$ | $\varepsilon$ |
| CALIBRATION VARIABLES $V_1$ $V_2$ $V_3$ $V_4$ $V_5$ $V_6$ $V_7$ | OIL TYPE 4 | $\rho$ | $\eta$ | $\varepsilon$ |
| | OIL TYPE 5 | $\rho$ | $\eta$ | $\varepsilon$ |
| | OIL TYPE 6 | $\rho$ | $\eta$ | $\varepsilon$ |
| | | ⋮ | ⋮ | ⋮ |
| | OIL TYPE N | $\rho$ | $\eta$ | $\varepsilon$ |

FIG. 2E

| TUNING FORK 1.1 TEMP. 40° C | APPROXIMATED FLUID CHARACTERISTICS | DENSITY | VISCOSITY | DIELECTRIC CONSTANT |
|---|---|---|---|---|
| | OIL TYPE 1 | $\rho'$ | $\eta'$ | $\varepsilon'$ |
| | OIL TYPE 2 | $\rho'$ | $\eta'$ | $\varepsilon'$ |
| | OIL TYPE 3 | $\rho'$ | $\eta'$ | $\varepsilon'$ |
| CALIBRATION VARIABLES $V_1'$ $V_2'$ $V_3'$ $V_4'$ $V_5'$ $V_6'$ $V_7'$ | OIL TYPE 4 | $\rho'$ | $\eta'$ | $\varepsilon'$ |
| | OIL TYPE 5 | $\rho'$ | $\eta'$ | $\varepsilon'$ |
| | OIL TYPE 6 | $\rho'$ | $\eta'$ | $\varepsilon'$ |
| | | ⋮ | ⋮ | ⋮ |
| | OIL TYPE N | $\rho'$ | $\eta'$ | $\varepsilon'$ |

460

FIRST CALIBRATION
$L_o, C_s, R_o, C_p$
464
VACCUM/AIR
(462)
SIGNAL (dB)
FREQUENCY (kHz)
(w)

474
470
SECOND CALIBRATION
A, B, k
KNOWN FLUID
(472)
SIGNAL (dB)
FREQUENCY (kHz)
(w)

FLUID UNDER-TEST
$\rho, \eta, \varepsilon.$
480

484
FLUID
UNDER-TEST
(482)
SIGNAL (dB)
FREQUENCY (kHz)
(w)

APPLICATION SPECIFIC INTEGRATED CIRCUITRY FOR CONTROLLING ANALYSIS OF A FLUID

CLAIM OF PRIORITY

This Application claims priority to U.S. Provisional Patent Application 60/419,404, filed on Oct. 18, 2002, and entitled "Machine Fluid Sensor and Method," which is incorporated by reference herein.

This U.S. Patent Application is also related to: (1) U.S. Patent Application No. 60/456,517, filed Mar. 21, 2003, entitled "Resonator Sensor Assembly," owned by the assignee of the present application and filed on the same date; and (2) U.S. Patent Application No. 60/456,767 filed, Mar. 21, 2003, entitled "Mechanical Resonator," owned by the assignee of the present application and filed on the same date.

BACKGROUND OF THE INVENTION

1. Field of the Invention

The present invention generally relates to fluid sensors, and more particularly to specialized circuitry for interfacing with a fluid sensor to enable control and monitoring of the fluid sensor to generate characterizing data for a fluid.

2. Description of the Related Art

In the art of fluid analysis, there exists a number of techniques for determining the characteristics of a fluid. In the case of fluids used in machines, such as automobiles, engines, and the like, there has been much experimentation in fluid analysis. For instance, a machine commonly requires specific fluids, and some are used to lubricate components of the machine. As is well known, one such fluid is engine oil, which is used to lubricate critical parts that would otherwise be damaged due to their continuous frictional movement.

To understand the state of a fluid at a particular point in time, sensors have been used to quantify characteristics of the fluid. Such sensors have included the use of resonating quartz-type sensors. The study of quartz-type sensors in the analysis of fluids, such as engine oil, has taken on many different avenues. The sensors come in all types of shapes, sizes, textures, operating frequency, etc. Depending on the characteristics targeted for sensing, the sensors are either shaped in a particular geometric design, coated with chemical layers, or arranged in arrays. Although prior art sensing techniques have taken on a wide array of forms, fluid sensing devices have largely been tested in a laboratory setting. In such a setting, the sensors can be connected to laboratory equipment to provide the necessary stimulus and detect the output from the sensor. The output from the sensor can be analyzed by the operator or caused to be processed by other computer programs to enable a user to determine whether or not the sensor detected appropriate data. If appropriate data is being generated, the data can be further interpreted to ascertain fluid characteristics.

As can be appreciated, this process, although computer assisted, is cumbersome and time consuming. Therefore, currently sensing technology, although able to sense some fluid characteristics, may not suffice in a commercial environment where on-the-fly or real-time in-situ measurements, analysis and feedback is needed. Such commercial applications may include, for instance, oil sensing applications. As mentioned above, such oil sensing applications can include, for example, engine oil sensing, oil drilling equipment sensors, and other applications where a fluid's characteristics need to be monitored and analyzed.

In view of the foregoing, there remains a need in the art for improved sensing methods and systems for analyzing fluids. In particular, there remains a need for specialized circuitry for interfacing with a sensor to enable control, receipt of sensed data, and processing of the sensed data to rapidly provide characterizing data for the fluid being sensed.

SUMMARY OF THE INVENTION

Broadly speaking, system and method is provided for monitoring quality parameters and level of a fluid used in the lubrication of a machine, such as a vehicle. In one aspect of the invention, a system and method is provided for determining the characteristics of a known machine fluid, and more specifically for monitoring the condition of a lubricant, e.g., engine oil. The present invention defines a communication interface between the sensor and the machine in which the fluid is to be monitored. In one embodiment, the communication interface is defined by an application specific integrated circuit (ASIC). The ASIC, in broad terms, incorporates circuitry for communicating with the sensor to initiate sensor activity, receive sensor output, process the sensor output, and communicate the sensor output to a user interface for presentation.

In one embodiment, a system for sensing characteristics of a fluid is disclosed. The system includes a tuning fork that is at least partially submerged in a fluid under-test and an application specific integrated circuit (ASIC). The ASIC includes analog input/output circuitry for providing stimulus to the tuning fork and receiving a response signal from the tuning fork. Conditioning circuitry for reducing analog signal offsets in the response signal and signal detection circuitry for identifying phase and amplitude data of the response signal are further provided as part of the ASIC. The ASIC further includes analog-to-digital conversion circuitry for converting the detected phase and amplitude data into digital form. Memory for holding calibration data and approximated fluid characteristics of the fluid under-test is integrated in the ASIC, wherein the digital form of the response signal is processed in conjunction with the calibration data and approximated fluid characteristics to generate fluid characteristics of the fluid under-test.

In another embodiment, a circuit for determining characteristics of a fluid under-test is provided. The circuit includes analog-to-digital processing circuitry for interfacing with a sensor and host electronics. The analog-to-digital processing circuitry includes a frequency generator for providing stimulus to the sensor and receiving a response signal from the sensor. Conditioning circuitry for reducing analog signal offsets in the response signal and signal detection circuitry for identifying phase and amplitude data of the response signal are provided. Further provided is analog-to-digital conversion circuitry for converting the detected phase and amplitude data into digital form. Memory for holding calibration data and approximated fluid characteristics of the fluid under-test is included in the circuitry. The digital form of the response signal is processed in conjunction with the calibration data and approximated fluid characteristics to generate fluid characteristics of the actual fluid under-test.

In yet another embodiment, a method for interfacing with a mechanical sensor to obtain characteristics of a fluid under-test is disclosed. The mechanical sensor is at least partially submerged in the fluid under-test. The method includes applying a variable frequency signal to the sensor and receiving a frequency response from the sensor. The frequency response is conditioned and components of the frequency response are detected. The method further includes converting the frequency response to digital form, such that the digital form is representative of the frequency response received from the sensor. Then, first calibration variables are fetched from memory. As used herein, the term "fetch" should be understood to include any method or technique used for obtaining data from a memory device. Depending on the particular type of memory, the addressing will be tailored to allow access of the particular stored data of interest. The first calibration variables define physical characteristics of the sensor. Second calibration variables are fetched from memory. The second calibration variables define characteristics of the sensor in a known fluid. The digital form is then processed when the sensor is in the fluid under-test, the processing uses the fetched first and second calibration variables to implement a fitting algorithm to produce fluid characteristics of the fluid under-test.

In still another embodiment, a method for interfacing with a tuning fork to obtain characteristics of a fluid under-test is disclosed. The tuning fork is configured to be at least partially submerged in the fluid under-test. The method includes applying a variable frequency signal to the tuning fork and receiving a frequency response from the tuning fork. The method also includes conditioning the frequency response, detecting signal components of the frequency response, and converting the frequency response to digital form. The digital form being representative of the frequency response received from the tuning fork. Then, the method fetches calibration variables for the tuning fork and processing the digital form of the response received from the tuning fork when in the fluid under-test, the processing being performed along with the fetched calibration variables and implementing a fitting algorithm to produce fluid characteristics of the fluid under-test.

In another embodiment, an application specific circuit (ASIC) for processing signals used to determine characteristics of a fluid under-test is disclosed. The ASIC is in communication with a tuning fork designed to operate a frequency that is less than 100 kHz. The ASIC includes circuitry for communicating a frequency signal to the tuning fork, circuitry for processing the a response signal received from the tuning fork into digital form, circuitry for storing calibration data for the tuning fork; circuitry for executing a fitting algorithm to ascertain characteristics of the fluid-under-test (the executing utilizing the calibration data); and circuitry for interfacing the ASIC circuitry that is external to the ASIC.

In summary, the present invention provides a sensing system that includes a mechanical resonator sensor and an ASIC that is employed for monitoring the level, condition, or both of a fluid. The sensing system is configured to include an input signal generator for exciting a mechanical resonator sensor, an ASIC for obtaining an output signal that corresponds with the response of the resonator to the input signal in the presence of a fluid during fluid monitoring. The sensing system may be further configured (e.g. as part of the ASIC or separate from it) to include a signal conditioner having at least one signal modifier for receiving the output signal, forming a conditioned signal in response thereto, and communicating the conditioned signal to a microprocessor unit. Though the signal generator, receiver and signal conditioner functions may be integrated into fewer components, divided among additional components, or split among a plurality of substrates, in a preferred embodiment, the functions are all performed by an assembly on a common substrate, namely a common integrated circuit.

As can be appreciated from the above, the present invention thus also contemplates a method for monitoring a machine fluid including the operations of placing a sensor including a mechanical resonator into a fluid reservoir, passageway, circulation system, resonating the sensor with an input signal while the resonator is in the reservoir, passage or circulation system, receiving an output signal from the sensor indicative of the response of the resonator to the fluid and the input signal, conditioning the output signal, and communicating the output signal to a processor. Optionally, a visual or audible indicator is triggered as a result of the output signal.

Other aspects and advantages of the invention will become apparent from the following detailed description, taken in conjunction with the accompanying drawings, illustrating by way of example the principles of the invention.

BRIEF DESCRIPTION OF THE DRAWINGS

The invention, together with further advantages thereof, may best be understood by reference to the following description taken in conjunction with the accompanying drawings.

FIG. 1A-2 illustrates another embodiment of the present invention, where the tuning fork is contained within a closed environment to ensure consistent measurement of a fluid under-test.

FIGS. 2D and 2E provide exemplary data that may be stored in the ASIC's memory, in accordance with one embodiment of the present invention.

DETAILED DESCRIPTION OF THE PREFERRED EMBODIMENTS

Figures 1, 1A:
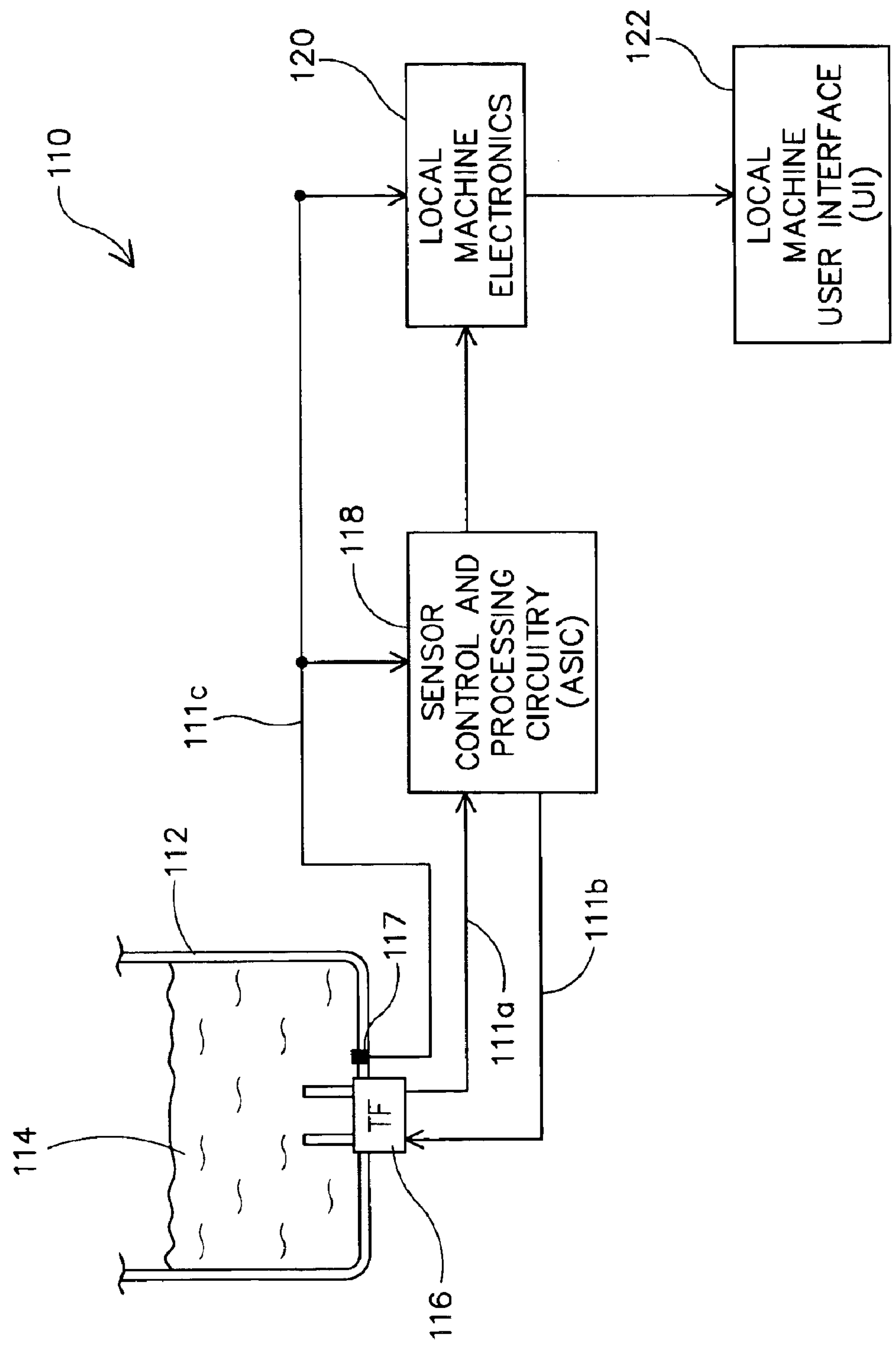
FIG. 1A-1 illustrates a fluid sensing system, in accordance with one embodiment of the present invention.

An invention is disclosed for an application specific integrated circuit (ASIC) that is used to interface with a fluid sensor to determine characteristic conditions of the fluid being sensed. As used herein, the fluid being sensed will be referred to as a "fluid under-test." Although specifics are provided with regard to engine oil, as the fluid under-test, it should be understood that any fluid capable of being sensed to ascertain its characteristics (e.g., chemical components or physical attributes) can utilize the teachings defined herein. For instance, the term "fluid" should be broadly construed to included any material in either a liquid form, gas form, a solid form, or a combination of any one of liquid, gas or solid.

Accordingly, in the following description, numerous specific details are set forth in order to provide a thorough understanding of the present invention. It will be apparent, however, to one skilled in the art that the present invention may be practiced without some or all of these specific details. In other instances, well known process steps have not been described in detail in order not to unnecessarily obscure the present invention.

Generally, the present invention provides a versatile fluid sensing system. More specifically, the present invention provides a fluid sensing system for machines that rely upon the presence, condition or both of a fluid to maintain efficient operation, such as (without limitation) a synthetic or natural engine oil. In an automotive application, the user is provided with the ability to determine the actual condition (e.g. or the relative deviation of the state of the engine oil from its initial or virgin state) of the engine oil at any particular time, including during operation. Alternatively, in conjunction with assessing fluid condition, the present invention may also be used to determine the amount of fluid remaining in a reserve of an assembly. This advantageously allows machine operators to extend the duration between fluid service events, while helping to assure continued operational integrity of a machine. Any dynamic assembly that depends on fluids to operate (e.g., where friction and heat are of a concern), will benefit from a system capable sensing the state of a fluid. For instance, the ability to dynamically monitor fluid condition, process data obtained from the monitoring, and report characteristics of the fluid to an interface or operator can have many applications. Assemblies that may benefit from the defined embodiments of the present invention are many, and can include without limitation, engines in general, automobiles, heavy machinery, military equipment, airplane parts, measurement while drilling, logging while drilling, exploration and production well logging tools, marine transportation, sub-sea exploration and aerospace related equipment, or any other fluid containing application. Still further, the fluid may be in a fluid refinery container, a fluid pipeline, or be the subject of testing and analysis. In one example, the fluid under-test may also be the subject of liquid chromatography.

In the automotive field, numerous components require lubrication, which is not limited to engine oil. For example, other automotive components may include the transmission, the transfer case, the differential, etc. Still further, the sensing system may further be used to determined the quality and amount of other fluids which are not necessarily used predominantly as a lubricant, including: brake fluids, steering fluids, antifreeze fluids, refrigerant fluids, windshield washer fluids, or any other fluid located in an automotive system.

In one embodiment, an oil sensing system is disclosed to determine the component characteristics and amount of engine oil. In an automotive application, the oil sensing system will provide a user, at a minimum, with a warning as to the need to change the oil (such as owing to the presence of contaminants, a breakdown or loss of useful ingredients or otherwise). In such an application, the warning is essentially informing the user of the automobile that the engine oil has reaches a quality level or condition that is lower than that recommend by the automobile's manufacturer (or set by the oil manufacturer).

The fluid sensing system preferably uses a mechanical resonator as the fluid sensor. The mechanical resonator is at least partially contained in the fluid under-test. To monitor the condition of the fluid under-test (i.e., engine oil), the mechanical resonator is provided with electrical energy through a frequency generator. The frequency generator is designed to apply a frequency signal (to the mechanical resonator) that is swept over a predetermined frequency range. Electronics are then used to detect the response signal from the mechanical resonator and process the signal to ascertain characteristics of the fluid under-test. In an embodiment of the present invention, the electronics are provided in the form of an application specific integrated circuit (ASIC).

FIG. 1A-1 illustrates a fluid sensing system 110, in accordance with one embodiment of the present invention. The fluid sensing system 110 utilizes a tuning fork 116 which can be placed into a fluid under-test 114. In simplest terms, the fluid may reside in a container 112. The container 112 can take on any form, such as a closed form, open form, pressurized form, etc., so long as it can hold the desired fluid. In a specific example, the fluid under-test 114 is engine oil. As shown, the tuning fork 116 is closely coupled to a temperature sensor 117 which provides feedback to electronics of the fluid sensing system 110. For example, the temperature sensor 117 may be a resistance temperature detector (RTD), or any other suitable temperature monitoring device. A sensor control and processing circuit 118 provides stimulus (e.g., such as an applied frequency) via connection 111*b* to the tuning fork 116. The response from the tuning fork 116 is received via connection 111*a* back to the sensor control and processing circuit 118. The response is an analog response of the tuning fork 116.

In one embodiment, the temperature sensor 117 is further interfaced via connection 111*c* to the sensor control and processing circuit 118. In specific embodiments, the connection 111*c* will also provide temperature data back to the local machine electronics 120. The connections 111 are provided to illustrate a functional interconnect between the tuning fork 116 and the temperature sensor 117, although it should be understood that fewer or more physical wires or connections may be used to complete the electrical interconnections. The local machine electrics 120 may be, for example, electronics of a machine containing the fluid under-test 114. In the automobile industry, specialized computers and electronic are commonly provided as native to an automobile, and such electronics and associated software operate to control and receive feedback from the various systems of the automobile. Accordingly, it is envisioned that the local machine electronics 122 can also make use of temperature data.

The temperature sensor 117 therefore will provide temperature data for the fluid under-test in a location that is closely coupled to the tuning fork 116, so that an accurate temperature near the tuning fork 116 can be obtained. The sensor control and processing circuit 118 may then use the temperature obtained from the temperature sensor 117 to process the signals.

Further, as the local machine electronics will receive the data processed by the sensor control and processing circuit 118, appropriate read-out to local machine user interface 122 can be made. Local machine user interface 122 may be a display on an automobile, may be a display on a read-out of a machine (analog or digital display), or may be a display of a computer that is local to the machine containing the fluid under-test 114.

Broadly speaking, the sensor control and processing circuit 118 is provided as circuitry that closely communicates with the tuning fork 116 to provide stimulus to the tuning fork, and also receive the response from the tuning fork and process the data received from the tuning fork into appropriate forms to be further processed by the local machine electronics 120. In a preferred embodiment, the sensor control and processing circuit 118 is provided in the form of an application-specific integrated circuit (ASIC). Accordingly, the local machine electronics 120 will be interchangeably referred to herein as the "ASIC 118."

In one embodiment, the ASIC 118 has the capability of generating a frequency signal that is provided through 111*b* to the tuning fork, and then is capable of receiving analog signals from the tuning fork over 111*a*. The analog signals received over 111*a* are then processed by the ASIC to extract information that will be used to identify characteristics of the fluid under-test 114. In one embodiment, the analog data is conditioned by the ASIC and then converted into digital form before being passed to the local machine electronics 120. Local machine electronics 120 will then communicate the detected characteristics of the fluid under-test to the local machine user interface 122.

Figures 1, 1A, 2:
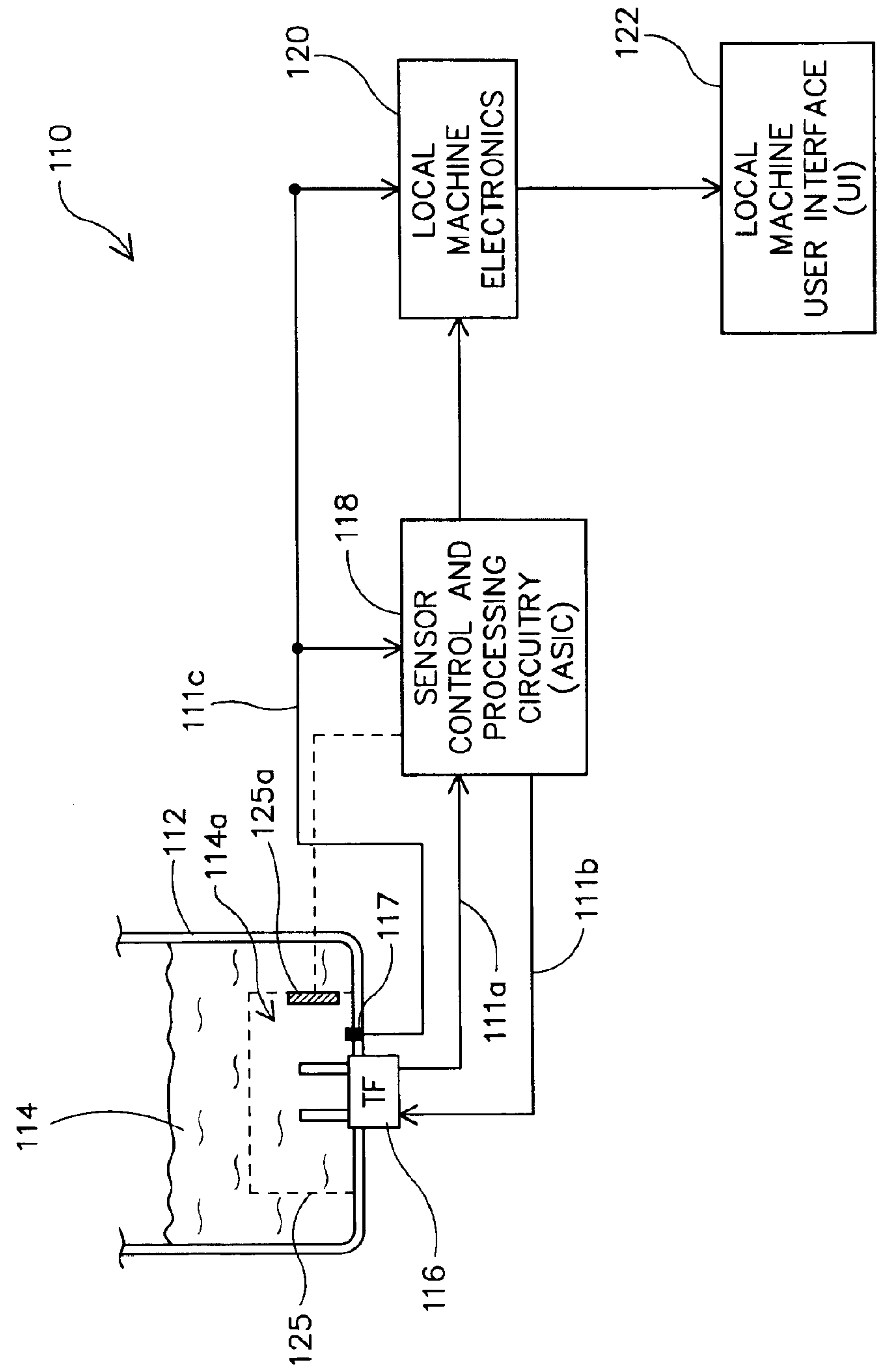

FIG. 1A-2 illustrates another embodiment, where the tuning fork is maintained in a closed environment 125 that will contain an amount of the fluid under-test 114*a*. As the condition of the fluid under-test fluctuates during operation of a motor, for example, it may be desirous to take in a sample 114*a* of the fluid under-test 114 and place it in a separate compartment that is maintained at a substantially constant temperature. To maintain the temperature at a particular level, a temperature controller 125*a* (e.g., a heating coil, a cooling system, etc.) can be used. The temperature controller 125*a* will thus maintain the temperature of the sample fluid under-test 114*a* consistently at a given temperature, which may be different than the fluid under-test 114 contained in the container 112 (e.g., oil pan of a motor). The temperature controller 125*a* can either operate alone, or can be controlled through a circuit or software. In one embodiment, the temperature controller 125*a* is coupled to the ASIC 118, which will include circuitry or firmware that will monitor the temperature and adjust the temperature as needed. In still another embodiment, the temperature controller 125*a* can be desired to lower the temperature fluctuation range, as opposed to allowing the fluid 114*a* to shift across the entire temperature spectrum of the entire fluid under-test 114.

Figure 1B:
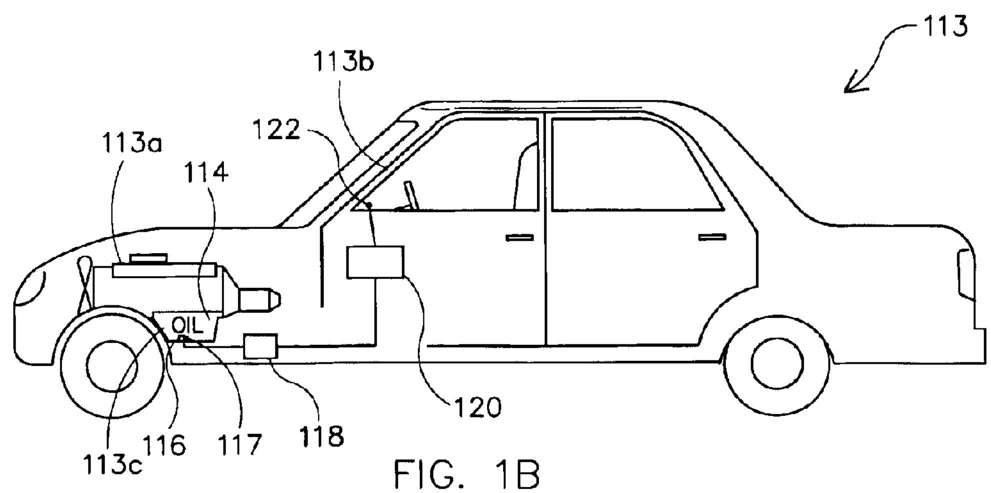
FIG. 1B illustrates an exemplary automobile incorporating the fluid sensing system, in accordance with one embodiment of the present invention.

FIG. 1B illustrates an automobile 113 having an engine 113*a* and a display dashboard 113*b*. The engine 113*a* will include an oil pan 113*c*, as is well known in the art. The oil pan 113*c* will have a tuning fork 116 inserted therein. The tuning fork 116 may be inserted at any location within the oil pan 113*c*, so long as the tuning fork tines are sufficiently in contact with the fluid under-test 114. The fluid under-test 114 is the oil contained within the oil pan 113*c*, in this example. The tuning fork 116 is shown coupled to the ASIC 118, in one embodiment.

The ASIC 118 is in turn coupled to the local machine electronics 120 that may be provided by the automobile 113 manufacturer. In operation, the tuning fork 116 will be contained within the oil pan 113*c* and the ASIC 118 will be integral with the tuning fork 116. In another embodiment, the ASIC will be located close to the tuning fork 116, but not integral therewith. In still another embodiment, the ASIC will be mounted to a printed circuit board that is connected to the automobile 113 (i.e., either with other local electronics or separate there from).

Irrespective of its physical installation, the ASIC 118 may continuously monitor the condition of the fluid under-test 114 and provide data to the ASIC 118. The ASIC 118 will therefore continuously communicate back to the local machine electronics 120 which then provides the information to the local machine user interface 122. In another embodiment, the monitoring will only be during a specific duration, at predetermined times, or on-demand (i.e., per user/technician request or query). In this example, the local machine user interface 122 will be provided in the form of a display dashboard 113*b* that provides visual, audible, or a combination of visual and audible information to a driver or user of the automobile 113. In this manner, the driver (or technician) of the automobile 113 will be informed of the condition of the fluid under-test 114 during the use/service of the automobile 113. In one example, when the fluid under-test, e.g., engine oil, becomes degraded to a level that may require replacement, the local machine user interface 122 will display an indication to the user of the automobile 113 by way of the display dashboard 113*b*.

In one arrangement, the tuning fork 116 may be a part of an oil drain plug. In this arrangement, the oil sensing system may be further configured with an actuator, sensor or combination thereof (e.g., magnetic sensor) that indicates if the tuning fork 116 (and hence the oil drain plug) has been placed in the oil drain hole. Such an indicator is particularly attractive to the extent that the insertion or removal and re-insertion of an oil drain plug typically coincides with the filling of or removal and re-filling of fluid from the engine. In this manner, the ability to provide a reference value for further comparison is readily enhanced. That is, upon insertion of the drain plug in the drain hole, the actuator, sensor or combination thereof will send a signal that effectively re-sets the system. As a result, A measurement can be taken of the fluid immediately upon its filling, which is expected to generally coincide with insertion of the drain plug, and a reference value established for the fluid (i.e., the fluid in its fresh state), which can be stored in memory associated with the system for later comparison.

Figure 1C:
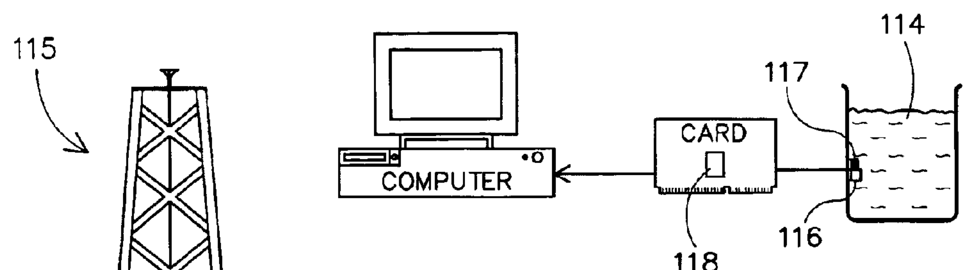
FIGS. 1C–1E provide further illustrative examples in which the fluid sensing system of the present invention can be used.

FIG. 1C illustrates an example where the ASIC 118 is connected to the tuning fork 116 and the temperature sensor 117 in a laboratory setting (or on a desktop where a fluid needs to be tested to identify its fluid characteristics). The fluid under-test 114 can then be analyzed using the ASIC 118 and a computer system. Still further, the ASIC 118 can be integrated onto a host card that can be installed onto the computer, using a standard bus interface (i.e., parallel bus, USB, IDE, SCSI, etc.). In another embodiment, a computer can be specifically integrated with the ASIC 118 so that a host card need not be installed onto the computer. In that situation, the tuning fork 116 and the temperature sensor 117 would be connected directly to the computer system and the computer system would provide the processing necessary to determine the characteristics of the fluid under-test 114. In still another embodiment, the ASIC 118 can be integrated into a handheld or portable device. Such a portable device can have many applications, such as laboratory applications, filed applications, factory applications, etc.

Figure 1E:
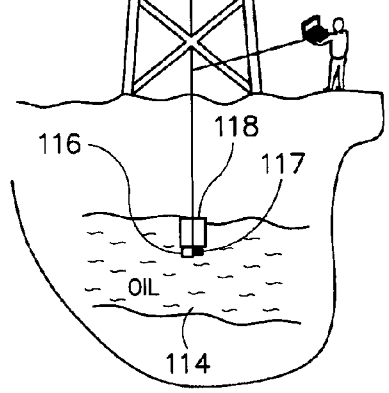
Figure 1D:
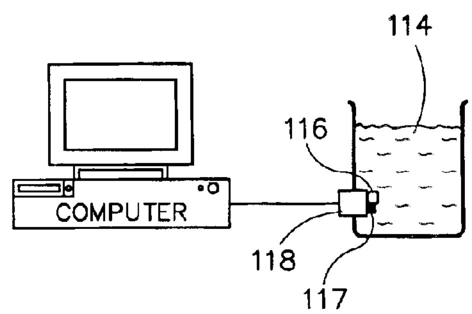

In yet another embodiment, FIG. 1C illustrates a laboratory setting where a computer is connected to the tuning fork 116 and the ASIC 118 is integrated with the tuning fork 116. The temperature sensor 117, in a similar manner, would be integrated closely to the tuning fork 116 so that appropriate temperature readings can be obtained near the tuning fork 116. In still another embodiment, the tuning fork 116, and temperature sensor 117 can be integrated with the ASIC 118 at a remote point in order to obtain fluid characteristic data from a fluid under-test 114. For instance, in an oil exploration site 115 of FIG. 1E, the tuning fork/ASIC can be used to identify the characteristics of oil that is intended for drilling. In a further example, the tuning fork/ASIC can be integrated directly into standard measurement while drilling, logging while drilling, exploration and production well logging tools, so that physical characteristics of oil and/or gas quality can be determined on-the-fly, as formation fluid is being pumped from a well. The results can then be provide back to a computer, such as a laptop computer (or a local measurement while drilling, logging while drilling, exploration and production well logging tool computer display), to provide instant information regarding physical characteristics of the oil or gas in and from the formation.

Figure 2A:
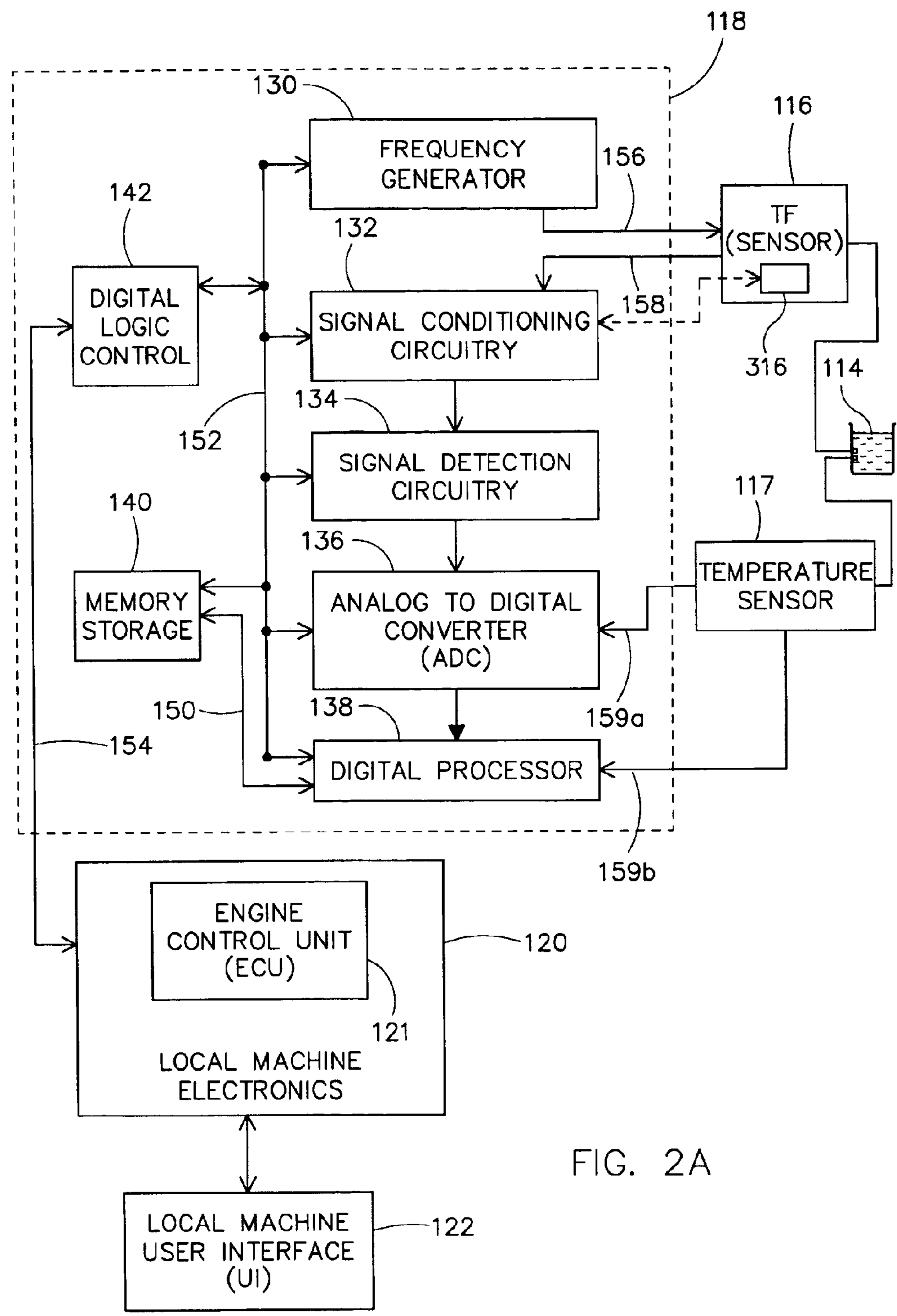
FIG. 2A illustrates a block diagram of an ASIC designed to provide stimulus to a tuning fork and receive and process data to provide information regarding the characteristics of a fluid under-test.

FIG. 2A illustrates a block diagram of the ASIC 118 and its components designed to provide stimulus to the tuning fork 116 and receive and process data to provide information regarding the characteristics of a fluid under-test. In one embodiment, the ASIC will include a frequency generator 130 that is configured to provide a frequency stimulus to the tuning fork 116 by way of communication line 156. The generated frequency is preferably a variable frequency input signal, such as a sinusoidal wave or square wave, that sweeps over a predetermined frequency range. The sweeping range will preferably include the resonance frequency range of the sensor. Preferably, the frequency is less than 100 kHz, and more preferably, is in the range of about 5 kHz and about 50 kHz, and most preferably, is in the range of about 20 kHz to about 35 kHz.

The tuning fork response over the frequency range is then monitored to determine the physical and electrical properties of the fluid under-test. The response from the tuning fork 116 is provided to a signal conditioning circuitry block 132, by way of a communication line 158. In one preferred embodiment, the tuning fork 116 will also include a capacitor 316, which will be described in greater detail below. The capacitor 316 is also coupled to the signal conditioning circuitry 132. The signal conditioning circuitry 132 is provided to receive the analog form of the signal from the tuning fork 116 and condition it so that more efficient signal processing may be performed before further processing.

The signal conditioning circuitry 132 will receive the analog output from the tuning fork 116, and is designed to substantially eliminate or reduce signal offsets, thus increasing the dynamic range of the signal that is to be further processed. In this manner, further processing can concentrate on the signal itself as opposed to data associated with the signal offset.

Signal detection circuitry (SDC) 134 is also provided, and it is coupled to the signal conditioning circuitry 132. Signal detection circuitry 134 will include, in one embodiment, a root mean squared (RMS) to DC converter, that is designed to generate a DC output (i.e., amplitude only) equal to the RMS value of any input received from the signal conditioning circuitry 132. The functional operation of a RMS-to-DC converter is well known to those skilled in the art. In another embodiment, the signal detection circuitry 134 may be provided in the form of a synchronous detector. As is well known, synchronous detectors are designed to identify a signal's phase and amplitude when preprocessing of an analog signal is desired in order to convert the analog signal into digital form. Once the signal detection circuitry block 134 processes the signal received from the signal conditioning circuitry 132, the signal detection circuitry 134 will pass the data to an analog-to-digital converter (ADC) 136. The analog-to-digital converter 136 will preferably operate at a sampling rate of up to 10 kHz while using a 10-bit resolution. The analog-to-digital converter (ADC) can, of course, take on any sampling rate and provide any bit resolution desired so long as the data received from the signal detection circuitry is processed into digital form.

The ADC 136 will also receive information from the temperature sensor 117 to make adjustments to the conversion from the analog form to the digital form in view of the actual temperature in the fluid under-test 114. In an alternative embodiment, the temperature sensor 117 can be omitted, however, the temperature sensor 117 will assist in providing data that will expedite the processing by the ASIC 118.

The digital signal provided by the analog-to-digital converter 136 is then forwarded to a digital processor 138. The digital processor 138 is coupled to memory storage 140 by way of a data bus 150 and a logic bus 152. Logic bus 152 is also shown connected to each of the frequency generator 130, the signal conditioning circuitry 132, the signal detection circuitry 134, and the analog-to-digital converter 136. A digital logic control 142 is directly coupled to the logic bus 152. The digital logic control 142 will thus communicate with each of the blocks of the ASIC 118 to synchronize when operation should take place by each one of the blocks. Returning to the digital processor 138, the digital processor 138 will receive the sensed data from the tuning fork 116 in digital form, and then apply an algorithm to identify characteristics of the fluid under-test 114.

The algorithm is designed to quickly identify variables that are unknown in the fluid under-test. The unknown variables may include, for example, density, viscosity, the dielectric constant, and other variables (if needed, and depending on the fluid). Further, depending on the fluid under-test 114 being examined, the memory storage 140 will have a database of known variables for specific calibrated tuning forks. In one embodiment, the memory storage 140 may also hold variables for approximation of variables associated with particular fluids. In another embodiment, the memory storage 140 will store serial numbers (or some type of identifier) to allow particular sets of data to be associated with particular tuning forks. In such a serial number configuration, the storage memory can hold unique data sets for a multitude of unique tuning forks. When a tuning fork is sold, for example, the purchaser need only input its assigned serial number into an interface, and the data set associated for that tuning fork will be used during operation. From time to time, it may be necessary to upload additional data sets to the storage memory 140, as new tuning forks (with unique serial numbers) are manufactured.

The process for using variable data from prior calibrations and from fluids that may closely resemble the fluid under-test, will be described in greater detail below. In general, however, the digital processor 138 may quickly access the data from the memory storage 140, and digitally process an algorithm that will generate and output variables that define the fluid under-test 114.

The digital processor will then communicate through the digital logic control 142 and communication line 154, the identified variables that characterize the fluid under-test 114 to the local machine electronics 120 (or some recipient computer, either locally or over a network). In one embodiment, the local machine electronics 120 will include an engine control unit (ECU) 121, that directly receives the data from the digital logic control 142 through signal 154. The engine control unit 121 will then receive that data and, in accordance with its programmed routines, provide feedback to the local machine user interface 122.

For example, the engine control unit 121, may set a different threshold for when the fluid under-test 114 (i.e., engine oil), has degraded. For example, different car manufacturers, and therefore, different engine control units for each car will define a particular viscosity, density and dielectric constant (or one or a combination thereof) that may be indicative of a need to change the oil. However, this programmable threshold level setting will differ among cars. Thus, the engine control unit 121 will provide the local machine user interface 122 the appropriate signals depending on the programming of the particular automobile or engine in which the engine control unit 121 is resident.

The ASIC 118 has been shown to include a number of component blocks, however, it should be understood that not all components need be included in the ASIC as will be discussed below. In this example, the digital processor 138 may be physically outside of the ASIC 118, and represented in terms of a general processor. If the digital processor 138 is located outside of the ASIC 118, the digital logic control 142 will take the form of glue logic that will be able to communicate between the digital processor 138 that is located outside of the ASIC 118, and the remaining components within the ASIC 118. In the automobile example, if the processor 138 is outside of the ASIC, the processor will still be in communication with the engine control unit 121.

Figure 2B:
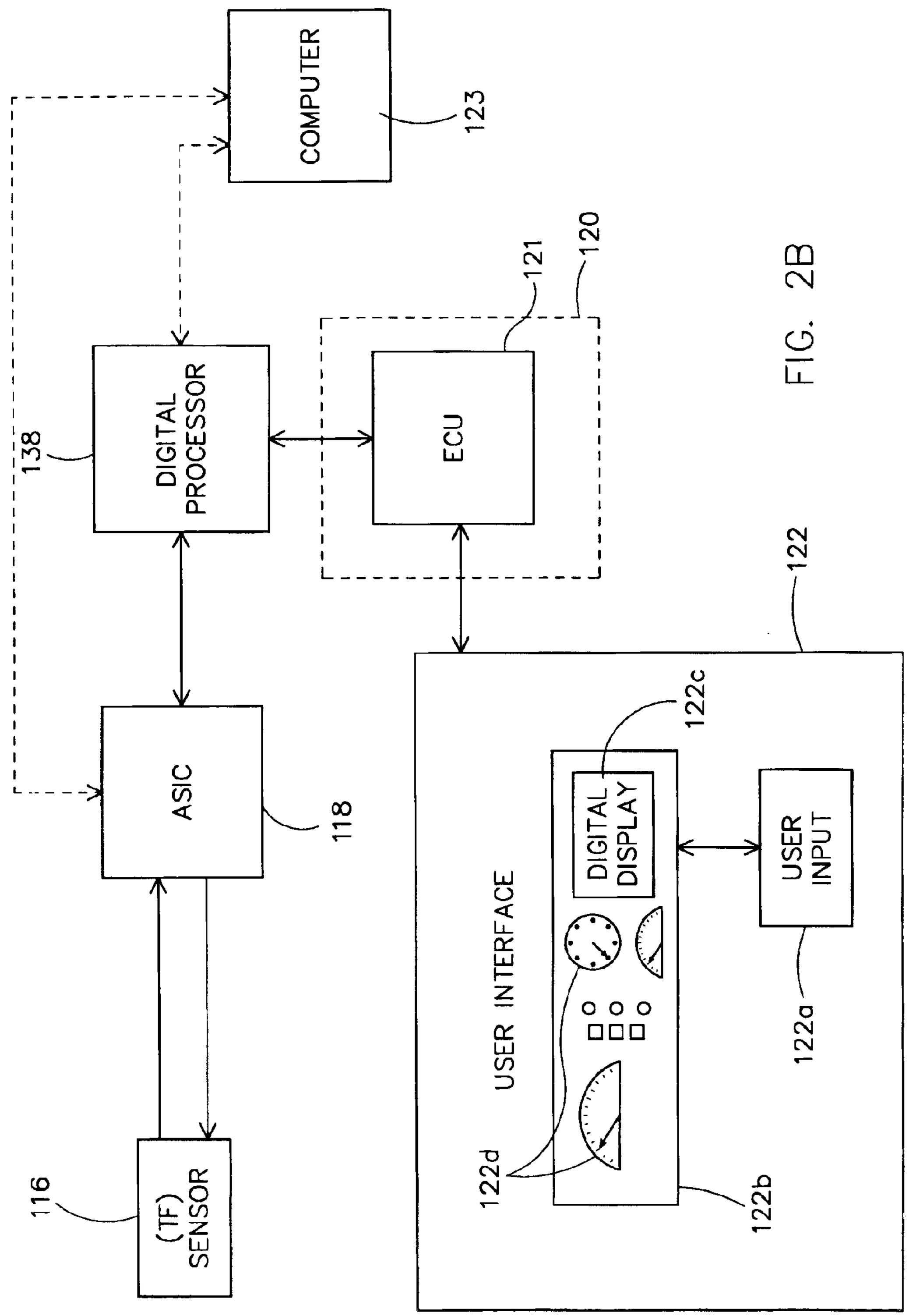
FIG. 2B illustrates an example where a digital processor is outside of the ASIC, in accordance with one embodiment of the present invention.

FIG. 2B illustrates an example when the digital processor 138 is outside of the ASIC 118. In such an embodiment, the digital processor 138 may be integrated into a printed circuit board that is alongside of the ASIC 118, or on a separate printed circuit board. In either case, the ASIC 118 will be in communication with the tuning fork 116 to provide stimulus and to process the received analog signals from the tuning fork 116. The ASIC will therefore convert the analog signals coming from the tuning fork 116 and convert them to a digital form before being passed to the digital processor 138.

If the ASIC 118 is provided on an automobile, and the digital processor 138 is outside of the ASIC 118, the digital processor 138 will still be able to communicate with the engine control unit 121 of the local machine electronics 120. The engine control unit 121 will therefore communicate with the local machine user interface 122. In this example, the user interface may include a user display 122*b*. The user display 122*b* may include analog and digital indicators 122*d*. The analog and digital indicators 122*d* may indicate the qualities of the fluid under-test (e.g., engine oil), and can be displayed in terms of a gauge reading to indicate to the user when the fluid under-test has degraded or needs to be changed.

In another embodiment, the user display 122*b* may include a digital display 122*c* (e.g., monitor) that may provide a digital output or display of the condition of the engine oil to the user through an appropriate graphical user interface (GUI). The user interface 122 may also include a user input 122*a*. The user input 112*a* may be a electronic interface that would allow a service technician, for example, to provide updated calibration information for a tuning fork that is inserted in a particular vehicle, or provide adjusted approximations for new engine oils that may just have come onto the market.

By way of the user input 122*a*, a service technician will be able to input new data to the ASIC 118 through the engine control unit 121. As mentioned above, the ASIC 118 will include a memory storage 140 for storing calibration data, and in some embodiments, storing approximated characteristics for fluids that may undergo sensing by tuning fork 116.

Figure 2C:
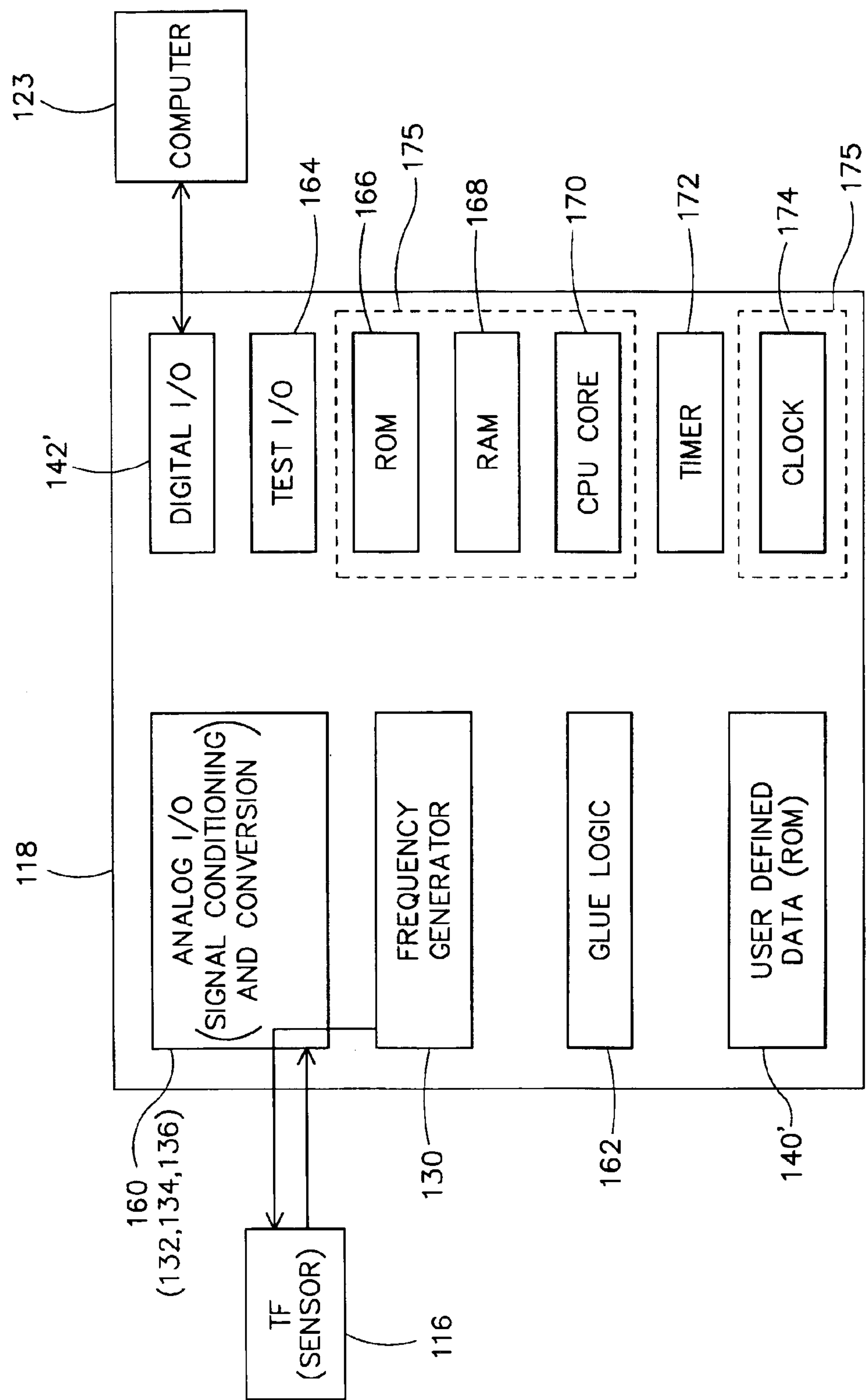
FIG. 2C illustrates another detailed block diagram of the ASIC, in accordance with one embodiment of the present invention.

FIG. 2C illustrates another detailed block diagram of the ASIC 118, in accordance with one embodiment of the present invention. In this example, the ASIC 118 shows a number of blocks that may be integrated into or kept out of, the ASIC 118. Blocks that may be kept outside of the ASIC include blocks 175. As a high level diagram, the tuning fork 116 is connected to an analog I/O 160. The analog I/O is representative of blocks 132, 134, and 136, in FIG. 2A above. The analog I/O block 160 therefore performs signal conditioning and conversion of the data received from the tuning fork 116.

Frequency generator 130, as discussed above, will provide the variable frequency input signal to the tuning fork 116 through the analog I/O 160. Glue logic 162 is provided to integrate together the various circuit blocks that will reside on the ASIC 118. As is well known, glue logic will include signaling lines, interfacing signals, timing signals, and any other circuitry that is needed to provide inputs and outputs to and from the chip that defines the ASIC 118. All such glue logic is standard and is well known in the art. The ASIC 118 further includes user defined data (ROM) 140'. As mentioned above, the user-defined data 140' may include calibration data, as well as approximated variable data for particular fluids that may become fluids under-test. The user defined data to be stored in this memory can come from any source. For example, the data may be obtained from a fluid manufacturer, a tuning fork manufacturer, a contractor party, etc. Still further, the data may be obtained in the form of a data stream, a database or over a network.

For example, FIGS. 2D and 2E provide exemplary data that may be stored within the user-defined data 140'. As shown in FIG. 2D, a tuning fork 1.1 (designated as such to emphasize varieties in tuning forks) may provide calibration variables, as well as approximated fluid characteristics for a particular type of fluid. In the example of FIG. 2D, the selected oil type 3 has approximated fluid characteristics for density, viscosity, and dielectric constant for a particular temperature, which is show to be 25° C. As used herein, the term "approximated fluid characteristics" represent starting point values of fluid characteristics before the fitting algorithm is started. Thus, the starting point values are initial values defined from experience, previous tests, or educated guesses. Consequently, the starting point values, in one embodiment, approximate the actual fluid characteristic values of the fluid under-test. In this manner, convergence to the actual fluid characteristics can be expedited.

In still another embodiment, it may be possible to start with the approximated fluid characteristics at some set of fixed values (which can be zero, for example). From each fixed value, the fitting algorithm can move the value until the actual fluid characteristic value is ascertained.

Continuing with the example, the approximated fluid characteristics for the same oil type 3 may have different approximated fluid characteristics due to the rise in temperature to 40° C., in FIG. 2E. The calibration variables will also be updated to reflect the values for a particular temperature for the tuning fork 1.1. As new oil types become available to the market, it may be necessary to update the approximated fluid characteristics for the different temperature ranges so that the user-defined data can be updated in the ASIC 118.

Referring back to FIG. 2C, a digital I/O 142' is provided to interface with a computer 123, and a test I/O interface 164 is provided to enable testing of the ASIC 118 during design simulation, during test bench testing, during pre-market release, and during field operation. The ASIC 118 will also include a timer 172 to provide coherent operation of the logic blocks contained in ASIC 118. As mentioned above, the ROM block 166, the RAM block 168, the CPU core 170, and the clock 174, can optionally be included in the ASIC 118 or removed and integrated outside of the ASIC 118. The ROM 166 will include programming instructions for circuit interfaces and functionality of the ASIC 118, the RAM 168 will provide the CPU core 170 with memory space to read and write data being processed by the CPU core 170, and the clock 174 will provide the ASIC with proper signal alignment for the various signals being processed by the blocks of the ASIC 118.

FIGS. 3A through 3D are provided to illustrate the flexibility of the component blocks contained within the ASIC 118. Groupings 200*a* through 200*d* show that the ASIC 118 can include less or fewer blocks, depending upon the application and location in which the ASIC will be integrated. For instance, if the ASIC is integrated on a computer in a laboratory setting, the ASIC may be provided with fewer blocks due to more processing by the host computer. If the ASIC is being integrated into a machine or product tool where no local computer is directly connected to the product or tool, the ASIC may include more components. However, it should be understood that the ASIC 118 by the illustration provided by groupings 200*a* through 200*d*, can be modularly integrated to include more or fewer functional blocks.

Figure 3A:
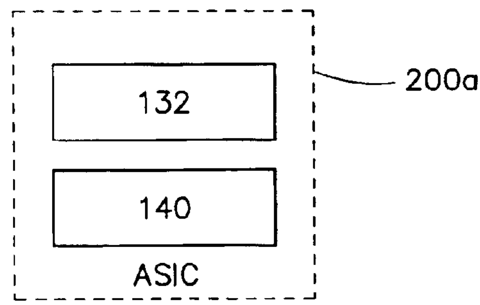
FIGS. 3A through 3D illustrate the flexibility of the component blocks that may be integrated in the ASIC, in accordance with one embodiment of the present invention.
Figure 3B:
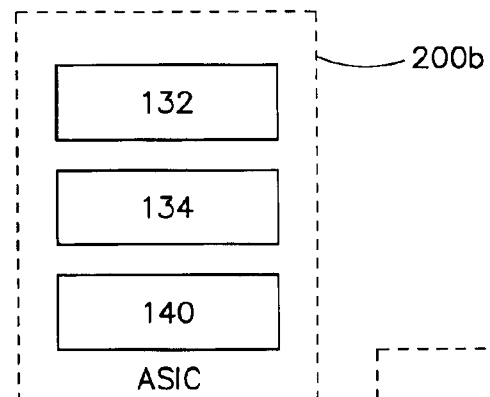
Figure 3C:
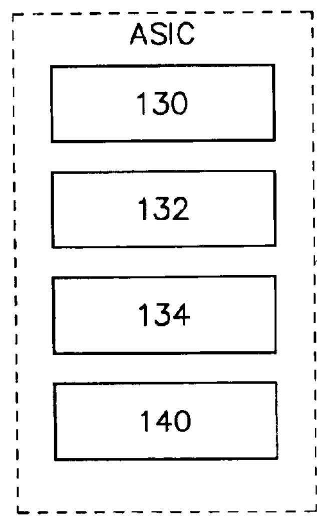
Figure 3D:
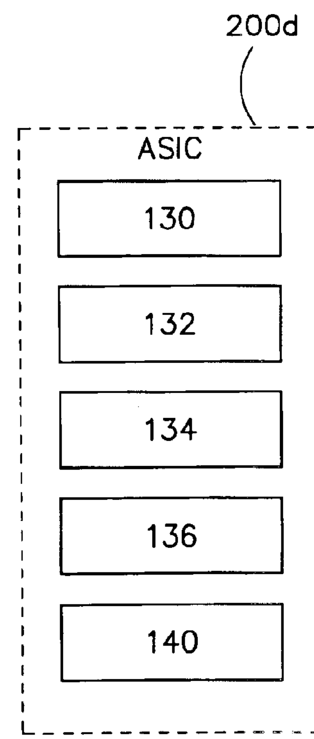

For completeness, FIG. 3A illustrates an ASIC with only the signal conditioning circuitry 132, and the memory storage 140. Of course, in each example provided herein, the ASIC will include glue logic and interfacing logic to interface the resulting ASIC to other circuitry. FIG. 3C illustrates an ASIC with a grouping 200*b* that includes the signal conditioning circuitry 132, the signal detection circuitry 134, and the memory storage 140. FIG. 3B illustrates an ASIC which has a grouping 200*c* that includes the frequency generator 130, the signal conditioning circuitry 132, the signal detection circuitry 134, and the memory storage 140. FIG. 3D illustrates a grouping 200*d* that includes the frequency generator 130, the signal conditioning circuitry 132, the signal detection circuitry 134, the analog-to-digital converter 136, and the memory storage 140. In each case, as mentioned above, associated glue logic and digital interfacing logic may be provided to interface with the resulting ASIC in accordance with the defined grouping.

Figure 4:
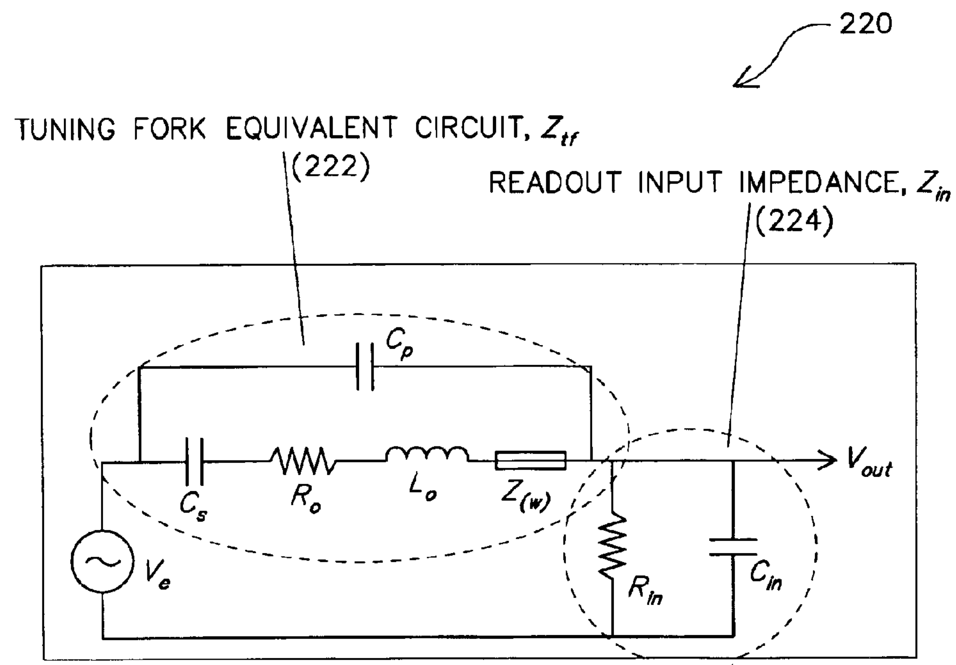
FIG. 4 illustrates a circuit diagram for a tuning fork equivalent circuit and a read-out input impedance circuit, in accordance with one embodiment of the present invention.

FIG. 4 illustrates a circuit diagram 220 for a tuning fork equivalent circuit 222 and a read-out input impedance circuit 224. The frequency generator is coupled to the tuning fork equivalent circuit 222 to a parallel connection of a capacitance Cp as well as a series connection of a capacitor Cs, a resistor Ro, an inductor Lo, and an equivalent impedance Z(ω). The read-out impedance circuit includes a parallel resistor Rin and a capacitor Cin. The output voltage is thus represented as Vout. The following equations define the equivalent circuit. In equation (2), the Vout of the equivalent circuit is defined. In equations (3) and (4), the impedance Zin and Ztf are derived. Equation (5) illustrates the resulting impedance over frequency Z(ω). As can be appreciated, the voltage Vout, graphed verses the frequency Z(ω), necessitates the determination of several variables.

The variables are defined in equation (1). In operation, the tuning fork's frequency response near the resonance is used to determine the variables that will define the characteristics of the fluid-under-test. The algorithm that will be used to determine the target fluid under-test characteristic parameters will require knowledge of data obtained during calibration of a tuning fork. In addition to access to calibration data, the algorithm will also utilize a data fitting process to merge approximated variables of the target fluid under-test, to the actual variable characteristics (i.e., density, viscosity, dielectric constant) for the fluid under-test.

$$\mathrm{Vout}(\mathrm{Co}, \mathrm{Cp}, \mathrm{Lo}, \mathrm{Cs}, \mathrm{Ro}, \mathrm{Z}(\omega), \mathrm{A}, \mathrm{B}, \rho, \eta, \omega, \in) \tag{1}$$

$$Vout(\omega) = \frac{Vo(Zin(\omega)}{(Zin(\omega) + Ztf(\omega)} \tag{2}$$

$$Zin=Rin^*(1/i\omega Cin)(Rin+1/i\ \omega Cin)^{-1} \tag{3}$$

$$Z_{tf}=(1/i\omega Cp)(Ro+1/i\omega Cs+i\omega Lo) \tag{4}$$

$$(1/i\omega Cp+Ro+1/i\omega Cs+i\omega Lo)^{-1}Z(\omega)=Ai\omega p+B^*(\omega\rho\eta)^{1/2}(1+i) \tag{5}$$

$$\in_{measured}=a+k^*Cp_{(measured)} \tag{6}$$

$$\varepsilon_{measured} = [\varepsilon_{cal} - (\varepsilon_{cal} - 1) * [Cp_{cal} / (Cp_{cal} - Cp_o)]] + [Cp_{(measured)} * [(\varepsilon_{cal} - 1) / (Cp_{cal} - Cpo_{(vacuum)})]] \tag{7}$$

$$a=[\in_{cal}-(\in_{cal}-1)^*[Cp_{cal}/(Cp_{cal}-Cp_o)] \tag{8}$$

$$k=[(\in_{cal}-1)/(Cp_{cal}-Cpo_{(vacuum)})] \tag{9}$$

$$\mathrm{Cp}_{(measured)} \text{ is a function of "k"} \tag{10}$$

In the circuit, it is assumed that $C_S$, $R_O$, $L_O$ are equivalent characteristics of a preferred resonator in a vacuum, $C_p$ is the equivalent parallel capacitance in a particular fluid under-test, ρ is the fluid density, η is fluid viscosity, ω is oscillation frequency. Cp is a function of k, as shown in equations (6) through (10). The constant "k" is, in one embodiment, a function of the tuning fork's geometry, and in one embodiment, defines the slope of a curve plotting ($Cp_{measured}$, $Cp_{cal}$, and $Cp_{vaccum}$) verses ($\in_{measured}$, $\in_{cal}$, and $\in_{vacuum}$), respectively. In a physical sense, the constant "k" is a function of the tuning fork's geometry, the geometry of the tuning fork's electrode geometry, the tuning fork's packaging (e.g., holder) geometry, the material properties of the tuning fork, or a combination of any of the above factors. The resulting value of Cp will be used to determine the dielectric constant E as shown by the equations.

Further, based on the below defined equations, it can be seen that viscosity and density can be de-convoluted by the following:

$$Z(\omega) = Ai\omega\rho + B\sqrt{\omega\rho\eta}\,(1+i)$$

$$Z(\omega) = i\omega\Delta L + \Delta Z\sqrt{\omega}\,(1+i)$$

$$\Delta L = A\rho,\ \Delta Z = B\sqrt{\rho\eta}$$

For some sensors, the value of $C_{p\ measured}$ is typically on the order of about 1 to 3 orders of magnitude greater than the value of $C_s$. Accordingly, in order to improve the ability to measure Z(ω), desirably trimming circuitry is employed as part of or in association with the signal conditioner, such as (without limitation), one or a combination of the illustrative trimming circuits of FIG. 6A, 6B, or 6D.

Figure 5:
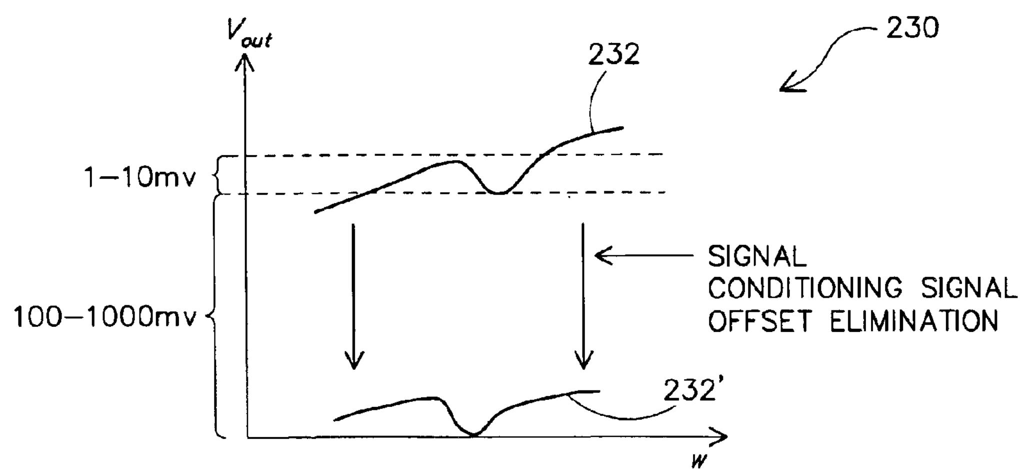
FIG. 5 is a graph that plots voltage (Vout) versus frequency ($\omega$), to illustrate a typical resonant frequency response, in accordance with one embodiment of the present invention.

FIG. 5 shows a graph 230 that plots voltage out (Vout) versus frequency (ω). As shown, the actual tuning fork response signal may produce a signal 232 that spans a particular frequency range. The frequency range will exhibit the signal having a resonance response that is indicative by the wiggle in the signal 232. The amplitude of the wiggle in the signal 232 may be in the range of about 1 mV to about 10 mV. However, the actual signal 232 produced by the tuning fork 116 will be at a signal offset that can be in the range of about 100 to about 1,000 mV, depending on the tuning fork characteristics and the fluid under-test.

In order to more efficiently process the signal being received from the tuning fork, the signal 232 is signal conditioned to eliminate or reduce the signal offset and thus, increase the dynamic range of the signal produced by the tuning fork. Thus, the data being analyzed can be more accurately processed. The conditioned signal is shown as signal 232' in FIG. 5. Exemplary techniques for conditioning the signal 232 to produce signal 232' will be illustrated with reference to FIGS. 6A and 6D below.

Figure 6A:
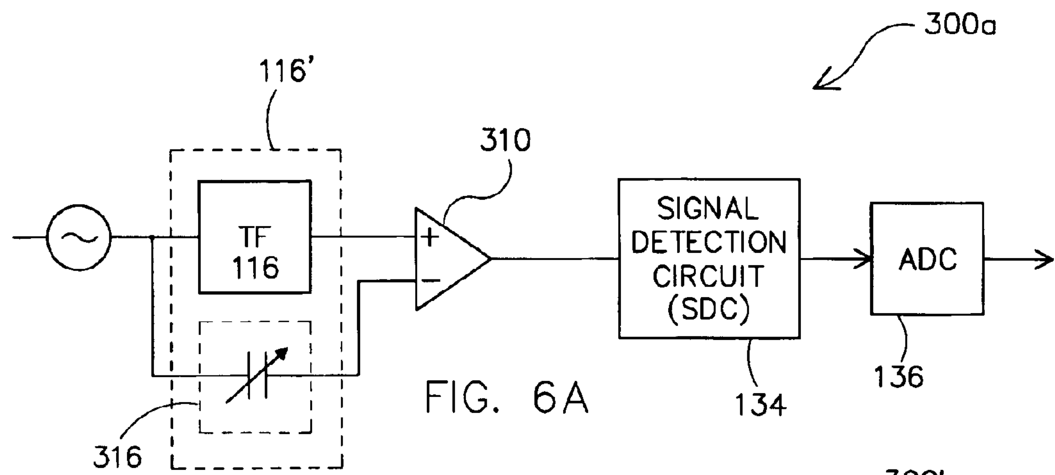
FIGS. 6A–6D illustrate exemplary techniques for conditioning the signal received from the tuning fork, in accordance with one embodiment of the present invention.

FIG. 6A shows a circuit 300*a* where an amplifier 310 receives input from the tuning fork 116, and input from a capacitor 316, in accordance with one embodiment of the present invention. The capacitor 316 is provided to assist in the signal conditioning that shifts the signal 232 of FIG. 5 to eliminate/reduce the signal offset and produce signal 232'. As shown, the frequency generator will provide the frequency stimulus to the tuning fork 116, and also to the capacitor 316.

The output from the capacitor 316 is provided to the negative terminal of the amplifier 310 and the output of the tuning fork 316 is provided to the positive terminal of the amplifier 310. The amplifier 310 will therefore provide an amplified signal which has been shifted due to the capacitance provided by capacitor 316, to a signal detection circuit (SDC) 134. The signal detection circuit will detect the phase and amplitude of the signal being output by the amplifier 310, and then provide the output to an analog-to-digital converter 136.

Figure 7:
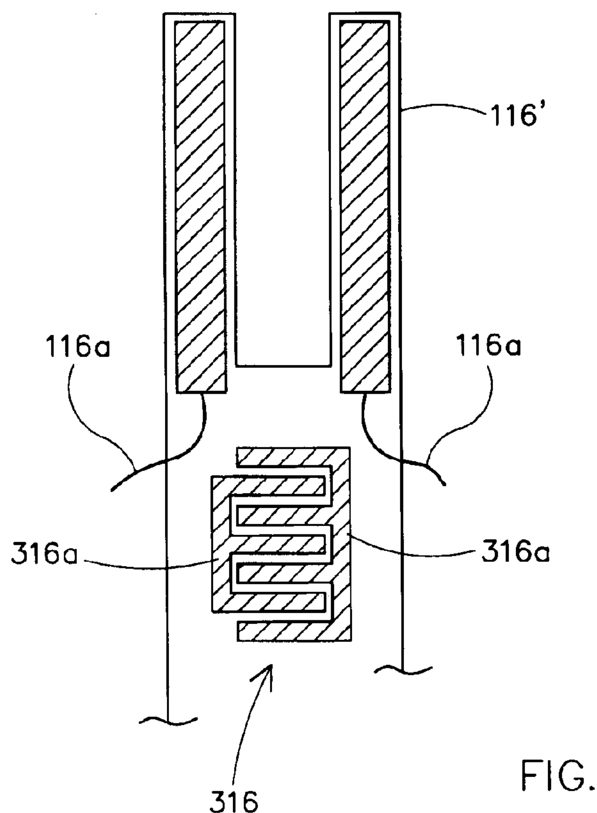
FIG. 7 illustrates the tuning fork with an integrated capacitor, in accordance with one embodiment of the present invention.

Capacitor 316, although shown to be variable, is in one embodiment, fixed to a particular level depending upon the shift necessary (or anticipated) to condition the received signal from the tuning fork 116. In one preferred embodiment, the tuning fork 116 may itself be configured to include the capacitor 316. An example where the capacitor 316 is integrated to the tuning fork 116 is shown in FIG. 7 below.

Figure 6B:
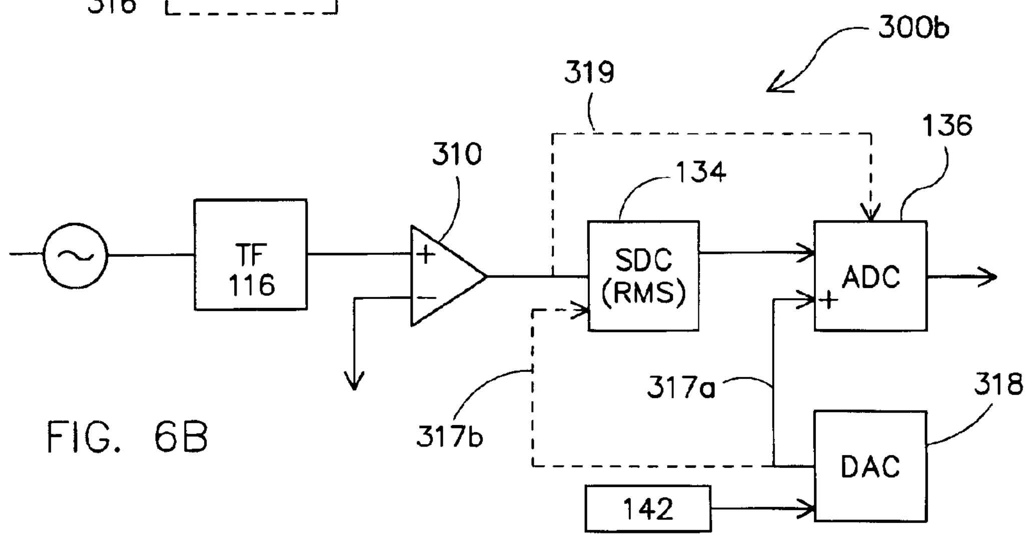

FIG. 6B illustrates a circuit 300*b* in which the tuning fork provides an input to an amplifier 310. The negative terminal of amplifier 310 is, in one exemplary embodiment, connected to ground. The output of the amplifier 310 is shown provided to the signal detection circuitry 134. In this embodiment, the signal detection circuitry 134 may be a root means squared (RMS) circuit that is configured to rectify the analog signal received from the amplifier 310. The output of the signal conditioning circuit 134 will then be output to the analog-to-digital converter 136, as in FIG. 6A.

In this embodiment, a digital-to-analog (DAC) converter 318 is provided to generate a compensating signal 317*a* to the analog-to-digital converter (ADC). The compensating signal will assist in providing the shift necessary to eliminate the signal offset as discussed with reference to FIG. 5. In an alternative embodiment, the digital-to-analog converter 318 will provide signal 317 directly to the signal detection circuit 134, as opposed to the analog-to-digital converter, and this option is illustrated by way of a dashed line 317*b*. The digital-to-analog converter 318 is, in this embodiment, designed to receive control from the digital logic control 142 as shown in FIG. 2A. In still another modification, the circuit 300*b* may be designed to exclude the signal detection circuit 134, and therefore provide the output of the amplifier 310 directly to the analog-to-digital converter 136 through a signal line 319. In such a case, the digital-to-analog converter 318 will provide its compensating signal directly to the analog-to-digital converter by way of signal line 317*a*. In this embodiment, the analog-to-digital converter 136 will be capable of detecting the signal and its appropriate phase and amplitude, thus eliminating the need for a signal detection circuit 134.

Figure 6C:
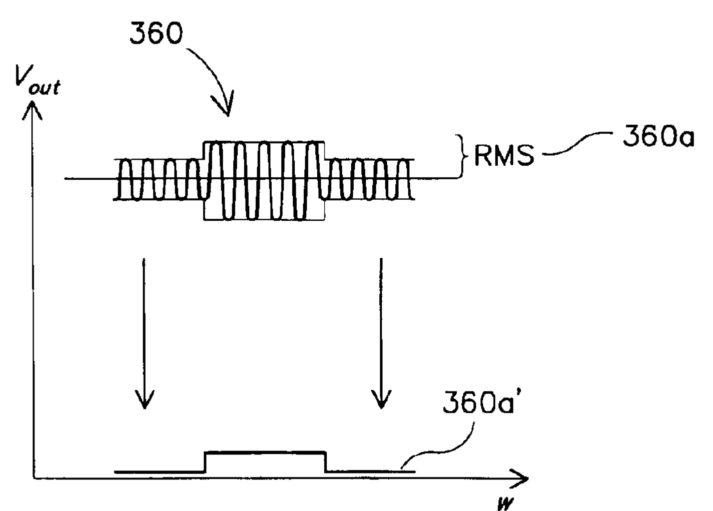

FIG. 6C illustrates a graph of voltage output versus frequency in which an analog signal is output from the tuning fork. The analog signal, in one embodiment, will be processed through the signal detection circuit (the RMS function of FIG. 6B), to generate a rectified signal 360*a*. The rectified signal is then conditioned by shifting it down to thus eliminate/minimize the signal offset by use of the digital-to-analog converter 318 of FIG. 6B. The resulting signal 360*a*' will therefore have a wider dynamic range which can be more efficiently processed by the digital circuitry that will apply the algorithm for determining the characteristics of the fluid under-test.

Figure 6D:
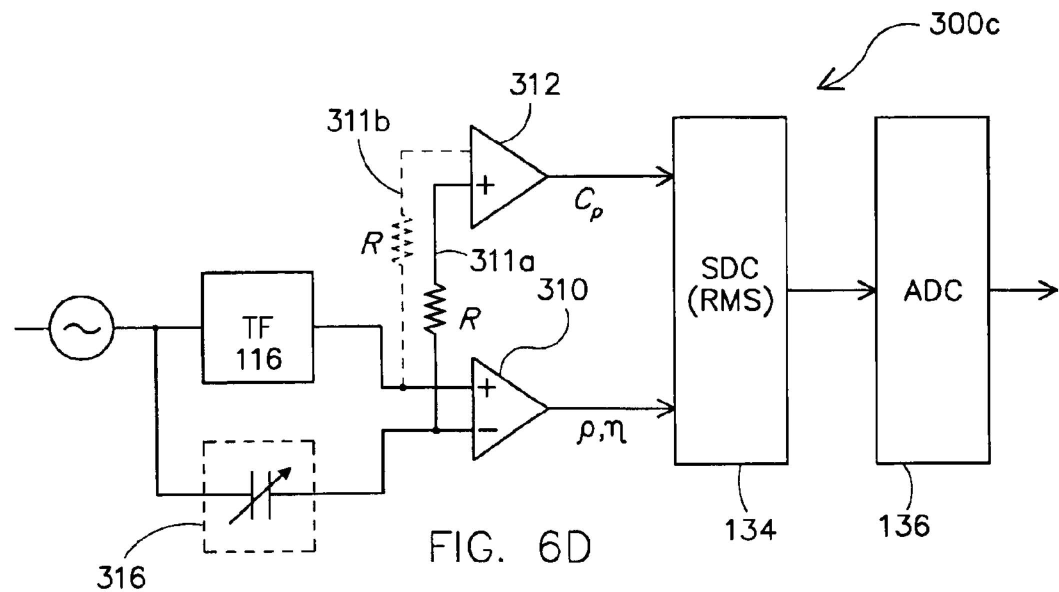

FIG. 6D illustrates yet another embodiment in which a circuit 300*c* provides signal conditioning before performing the analog-to-digital conversion in block 136. In this example, the tuning fork 116 and the capacitor 316, are couple to a differential amplifier 310. The differential amplifier 310 is capable of generating an amplified signal that is well represented of variables associated with density and viscosity, however, the capacitance of the fluid under-test (Cp) is a value that may be eliminated during the processing by the differential amplifier 310. For this reason, a summation amplifier 312 may be provided, and is connected 311*a* by way of a resistor to the negative terminal that couples to the capacitor 316, to thus produce data representative of Cp. In another embodiment, an additional connection may be made to the output of the tuning fork and the positive input of the differential amplifier 310. Thus, connection 311*b* will provide additional sensitivity and data for generating an appropriate Cp for the fluid under-test.

The analog signals coming from both the summation amplifier 312 and a differential amplifier 310 will be provided to the signal detection circuit 134, which will identify the appropriate phase and amplitude for the signals being output from the amplifiers. The signal detection circuit 134 will then output the data to the analog-to-digital converter 136.

FIG. 7 illustrates a tuning fork 116' in which a capacitor 316 has been integrated directly onto the surface of the tuning fork 116'. Tuning fork 116', as defined above, will include electrodes 116*a* and the capacitor 316 will include capacitor electrodes 316*a* that are capable of reading a capacitate charge to enable the tuning fork to itself, provide the offset necessary to condition the signal and provide the shift described with reference to FIG. 5. Thus, the tuning fork itself will provide the necessary elimination/reduction of the signal offset. The capacitor 316, in one embodiment, will be trimmed/set by the manufacturer to provide a capacitate value that is approximately capable of providing the necessary offset. In another embodiment, the capacitor can be of a form that will enable trimming after manufacturing.

One preferred tuning fork resonator of the present invention has one or more tines including a piezoelectric material and at least one electrode (or suitable structure for receiving the electrode) connected to the piezoelectric material. A performance-tuning material or other functionality optionally may also be included on the base material.

The use of a metal is most preferred for the electrodes. However, other conductive materials may also be employed, such as conductive polymers, carbon or otherwise. Preferred metals are pure metals or alloys including a metal selected from gold, platinum, silver, chromium, aluminum or mixtures thereof. Other noble or transition metals may also be employed.

The base materials of the resonators of the present invention preferably are selected from at least one type of device of piezoelectric materials, electrostrictive materials, magetostrictive materials, piezoresistive materials, elasto-optic materials, anisotropic materials, or combinations thereof. By way of example, the particular material may be a metallic material, a crystalline material, a ceramic material or a combination thereof. Examples of suitable materials include, without limitation, quartz, lithium niobate, zinc oxide, lead zirconate titanate (PZT), gallo-germanates (e.g., Langasite ($La_3Ga_5SiO_{14}$), Langanite, or Langatate), diomignite (lithium tetraborate), bismuth germanium oxide or combinations thereof. The preferred base materials may be undoped or doped with art-disclosed dopants.

Preferably the dimensions of the resonators for use in accordance with the present invention are such that the total volume of the resonator including the performance-tuning material is less than about 75 $mm^3$, more preferably less than about 50 $mm^3$, still more preferably less than about 25 $mm^3$, and even still more preferably less than about 15 $mm^3$. One preferred resonator has tines that do not exceed about 15 mm in its longest dimension, and more preferably is smaller than about 8 mm in its longest dimension. A preferred resonator has a thickness no greater than about 2 mm, and more preferably no greater than about 1 mm. By way of example, without limitation, one illustrative resonator is about 0.5×3×5 mm in dimension. Of course, larger resonators may also be employed. In one embodiment, a size of the tuning fork 116 is smaller than a wave length of an acoustic wave.

Examples of particularly preferred performance-tuning materials include one or a combination of two or more materials selected from the group consisting of polymers, ceramics, diamond, diamond-like carbon (e.g., Diamonex® DLC), and combinations thereof. For example, preferred performance-tuning materials might include one or a combination of two or more materials selected from the group consisting of fluoropolymers, silicones, polyolefins, carbides, nitrides, oxides, diamond, diamond-like carbon, and combinations thereof; and even more particularly might include one or a combination of two or more materials selected from the group consisting of polytetrafluoroethylene, fluorosilicone, polyethylene (e.g., high density polyethylene), polypropylene (e.g., high density polypropylene), silicon carbide, silicon nitride, diamond, diamond-like carbon, and combinations thereof. It is also possible that a material selected from the above identified examples of base materials may be employed as a performance tuning material.

Figure 8:
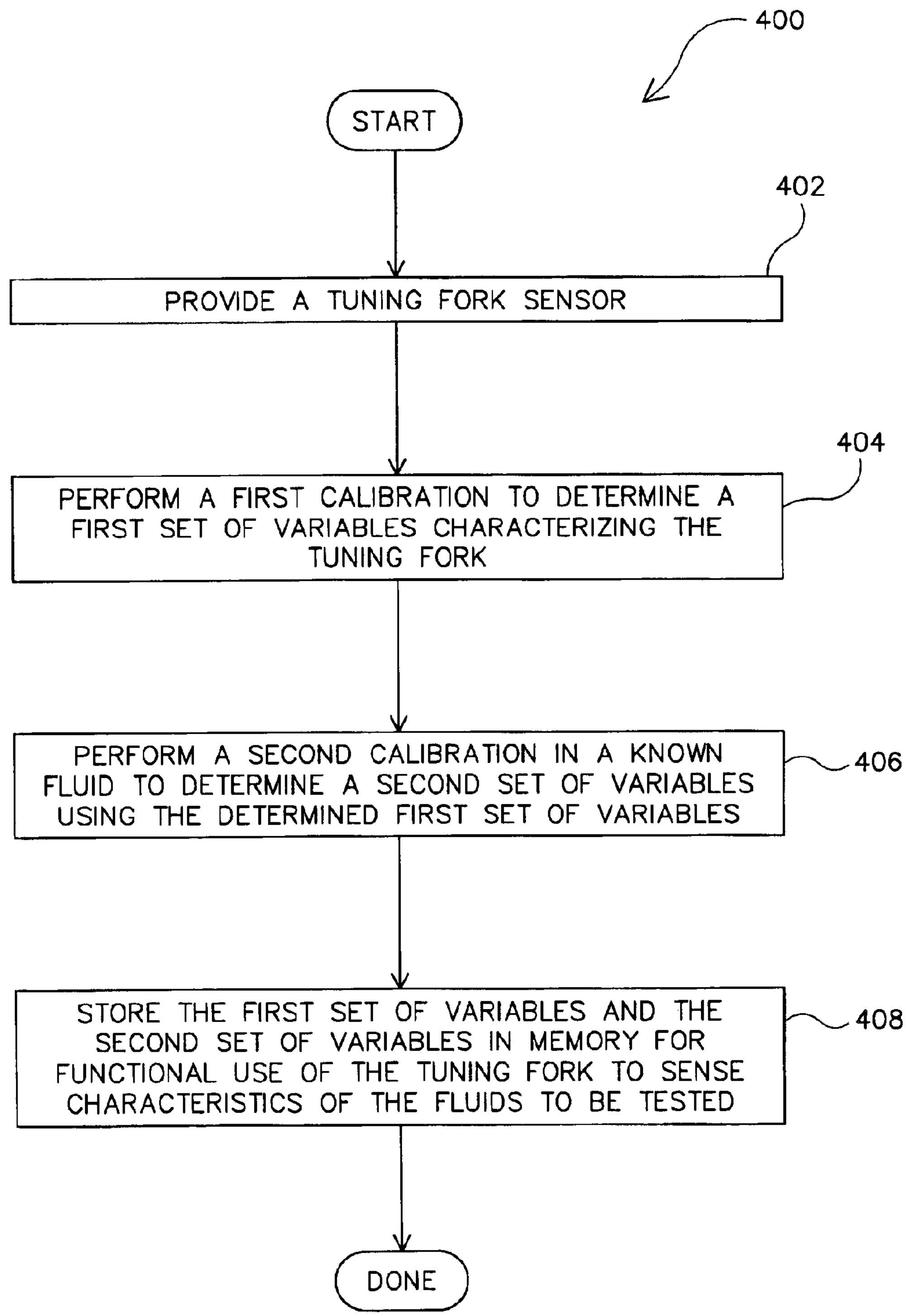
FIG. 8 is a flow chart diagram depicting method operations performed to calculate calibration data for a tuning fork, in accordance with one embodiment of the present invention.

FIG. 8 illustrates a flowchart diagram 400 depicting method operations performed to calibrate a tuning fork and obtaining variables characterizing a tuning fork, in accordance with one embodiment of the present invention. The method begins at operation 402 where a tuning fork sensor is provided. As mentioned above, the tuning fork sensor is preferably designed to be inserted into a fluid under-test to determine properties of the fluid. In one embodiment, the tuning fork sensor will be provided with electrodes to enable application of a variable frequency input signal over a predetermined frequency range to obtain a frequency-dependent resonator response. The method now moves to operation 404 where a first calibration to determine a first set of variables characterizing the tuning fork, is performed. The first calibration includes subjecting a tuning fork to vacuum or air to determine the response of the tuning fork and calibrate it against a known resonance frequency response.

Figure 11A:
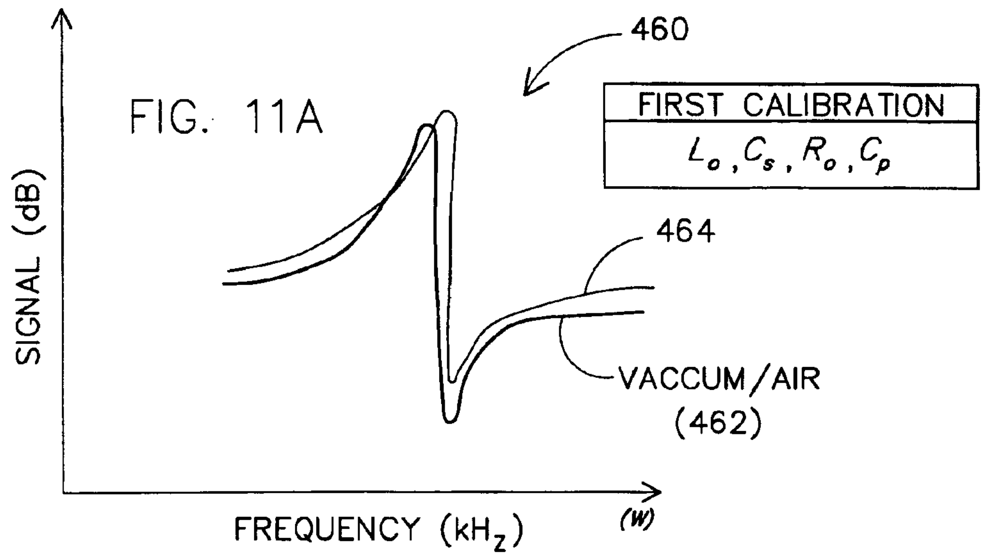
FIGS. 11A–11C illustrate plots for calibration and actual examination of a fluid under-test, in accordance with one embodiment of the present invention.

FIG. 11A illustrates an example of a known frequency response of the tuning fork in vacuum or air as shown by signal 462. Starting from an approximated signal 464 for the tuning fork in air, a fitting algorithm is executed to fit the approximated signal 464 to the signal 462. In performing this first calibration, it is possible to ascertain variables such as the inductance (Lo), the capacitance (Cs), the resistance (Ro), and the parallel capacitance (Cp) of the tuning fork in the medium. As the tuning fork is subjected to vacuum or air the impedance of the fluid, $Z(\omega)$ will be equal to zero.

Figure 11B:
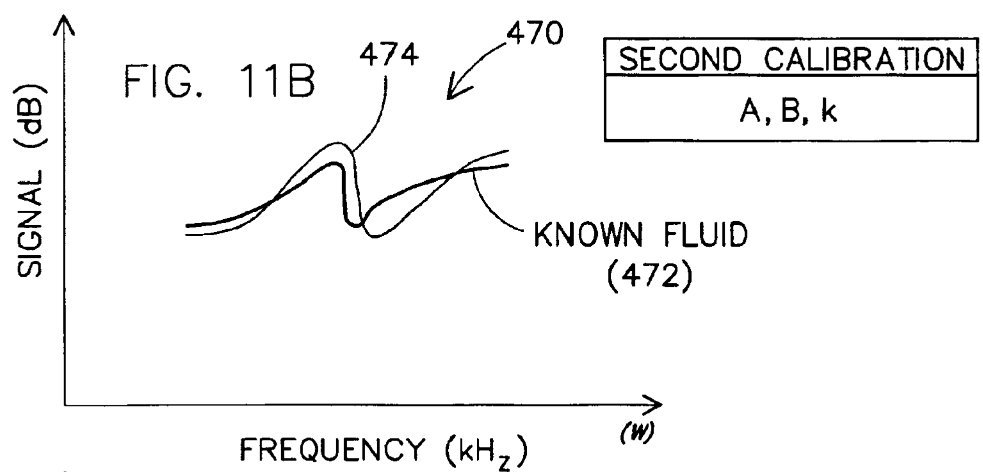

Accordingly, the first calibration will generate the first set of variables characterizing the actual tuning fork itself, as shown in the first calibration in FIG. 11A. Returning to FIG. 8, the method then moves to operation 406 where a second calibration in a known fluid is performed to determine a second set of variables. The second calibration will use the determined first set of variables from the first calibration. Reference is now made to FIG. 11B in which a second calibration is performed. In the second calibration, the frequency response will be provided for a known fluid as shown by signal 472. Beginning with an approximated signal for the known fluid 474, the calibration will take place such that signal 474 fits the known fluid signal 472. In performing the curve fitting operation, the second calibration will use the first calibration variables from FIG. 11A, to obtain the second set of variables which include A, B, and k. In one embodiment, the known fluid used in the second calibration will preferably be a volatile fluid so that contamination of the tuning fork will be maintained at a minimum. That is, it is a desire prevent the tuning fork from collecting or building up residues on the tines, before actual fluid under-test variable determinations are made using the same tuning fork. In one example, the known fluid may be carbon tetrachloride ($CCl_4$), alcohol, fluorinated solvents, ethanol, methanol, toluene, menthol ether ketone, hexane, heptane, isopropyl alcohol (IPA), etc. Still another calibration fluid may be deionized water (DIW) or other fluids that will not leave or only leave minimal residues on the tuning fork.

Returning again to FIG. 8, once the second calibration has been performed in operation 406, the method will move to operation 408 where the first set of variables and the second set of variables are stored in memory for functional use of the tuning fork in sensing characteristics of a fluid to be tested. In one embodiment, the first set of variables and the second set of variables are stored in the memory storage 140 or the user-defined data ROM 140', as discussed with reference to FIGS. 2B and 2C. Broadly speaking, the first calibration and the second calibration data will be performed on a tuning fork for a range of temperatures as shown in FIGS. 2D and 2E. The range of temperatures may vary between about 1 Kelvin and about 1000 Kelvin. In another embodiment, the range may be between about 77 Kelvin and about 600 Kelvin, and in still another embodiment, the range may be between about 233 Kelvin and about 423 Kelvin. Such ranges will vary depending on the application. These calibration variables from the first calibration and the second calibration, will therefore be stored in memory and can be recalled by the ASIC when processing a fluid under-test to ascertain characteristics of the fluid under-test, such as the density, viscosity, and the dielectric constant. In still another embodiment, the calibration variables may be stored on a removable storage media. When the calibration variables are stored on a removable storage media, the calibration data will be linked to a particular tuning fork. Accordingly, when a tuning fork is supplied to an end user, the end user may also be provided with the removable storage media (e.g., card, chip, memory stick, etc.) so that the appropriate calibration variables can be loaded onto or accessed by the ASIC for operation of the tuning fork. By storing the calibration variables in a removable storage media, it is also possible to continually update and refine the calibration variables for new tuning forks, and also provide the latest calibration data to end users when new tuning forks are provided for sale.

Still further, a particular embodiment may include the sale of a particular tuning fork and calibration variables for the tuning fork as a package. The calibration variables may also be stored on a magnetic card and the card can then be inserted into a computer or the local machine user interface by a technician to load the current calibration data for a particular tuning fork that is being installed in a particular machine. From time to time, it will be possible to update the calibration data for a tuning fork through the local machine user interface, by a technician, for example. Updates can also be provided to local electronics over a wireless link, over the Internet, etc. In one embodiment, the calibration data can be compactly stored, and provided in digital form is as little space as 64 bytes. Of course, the data size can increase or decrease depending on the needs.

Figure 9:
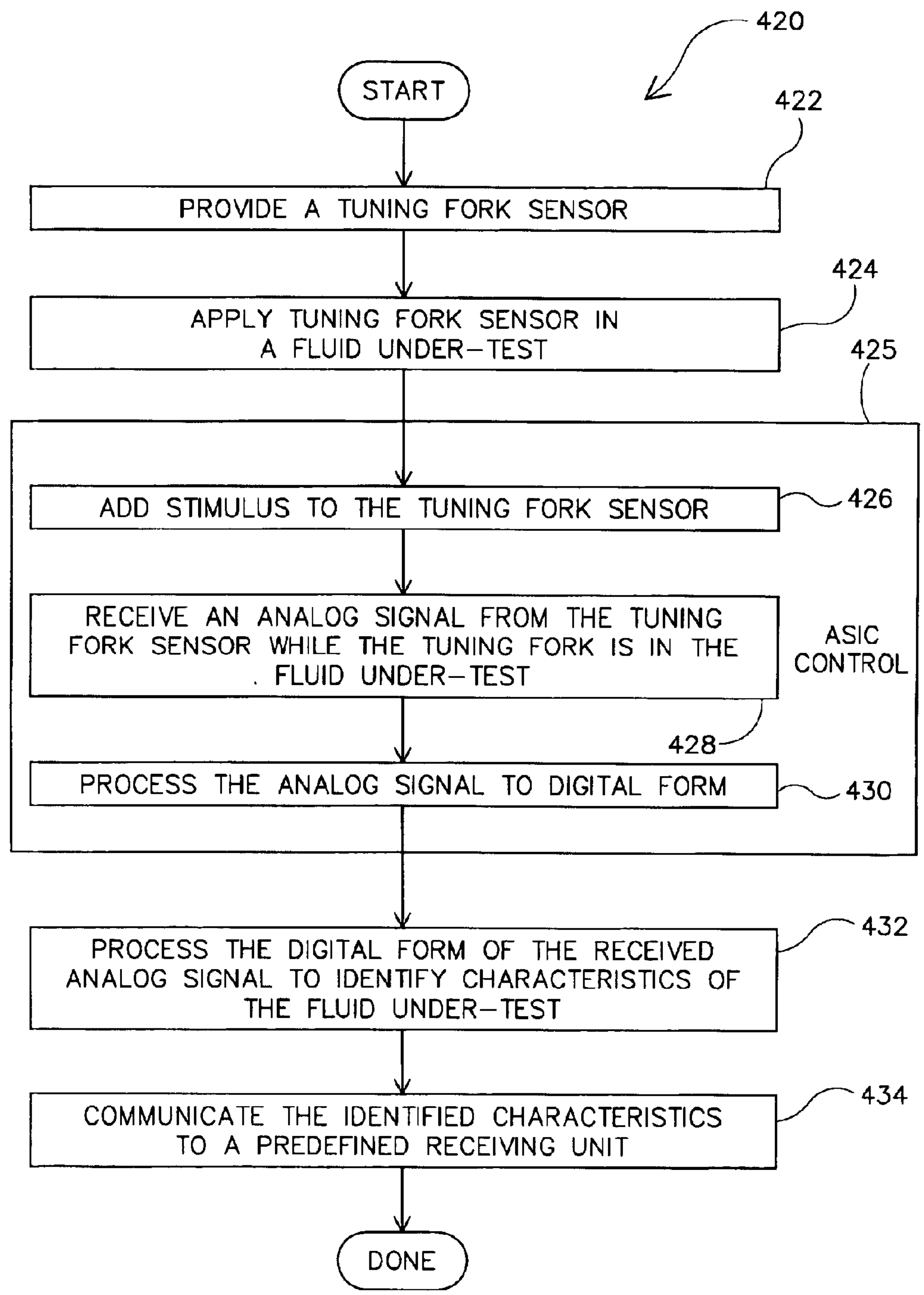
FIG. 9 is a flow chart diagram depicting method operations for controlling signals to a tuning fork, and receiving and processing signals in an ASIC to determine characteristics of a fluid under-test, in accordance with one embodiment of the present invention.

FIG. 9 illustrates a flowchart diagram 420 in which an ASIC is used to control activation of a tuning fork and also process the response from the tuning fork to enable communication of the response data in digital form. The method begins at operation 422 where a tuning fork sensor is provided. Once the tuning fork sensor has been provided, the method moves to operation 424 where the tuning fork sensor is applied into a fluid under-test. Applying the tuning fork sensor into a fluid under-test may include submerging a portion of the tuning fork (i.e., at least a portion of the tines) into the fluid under-test to enable the tuning fork to resonate within the fluid to be tested.

Once the tuning fork sensor has been applied to the fluid under-test, the method moves to operation 426. In operation 426, stimulus is applied to the tuning fork sensor. As mentioned above, the stimulus will be a frequency input signal that is varied over a frequency range and applied to the tuning fork sensor, to obtain a frequency-dependent resonator response. Preferably, the applied frequency will be less than about 100 kHz. The ASIC will then receive an analog signal from the tuning fork sensor while the tuning fork is in the fluid under-test in operation 428. Once the ASIC receives the analog signal from the tuning fork sensor, the method moves to operation 430, where the analog signal is processed into digital form.

As mentioned above, the ASIC will preferably include signal conditioning circuitry for receiving the analog signal, signal detection circuitry for detecting components of the signal being obtained from the tuning fork sensor, and an analog-to-digital converter to move the analog signal data into digital form. The method now moves to operation 432 where the digital form of the received analog signal is processed to identify characteristics of the fluid under-test.

In one embodiment, the processing of the digital form received from the analog signal, may also be performed by the ASIC in block 425. In an alternative embodiment, as mentioned above, the processing of the digital form may be performed outside of the ASIC as shown in FIG. 2B. In either embodiment, the digital form is then processed to identify characteristics of the fluid under-test. As will be discussed with reference to FIG. 11C, the characteristics of the fluid under-test being identified may include density, viscosity, and the dielectric constant of the fluid under-test. Once the characteristics have been identified in operation 432, the method will move to operation 434 where the identified characteristics are communicated to a predefined receiving unit. The predefined receiving unit may include a computer of a vehicle, a computer in a laboratory, a storage device, a remote computer receiving data over the Internet (by connected wires or wireless), or any other receiving unit desiring to receive information regarding the fluid under-test. Once the identified characteristics have been communicated to the predefined receiving unit, the method will end.

Figure 10:
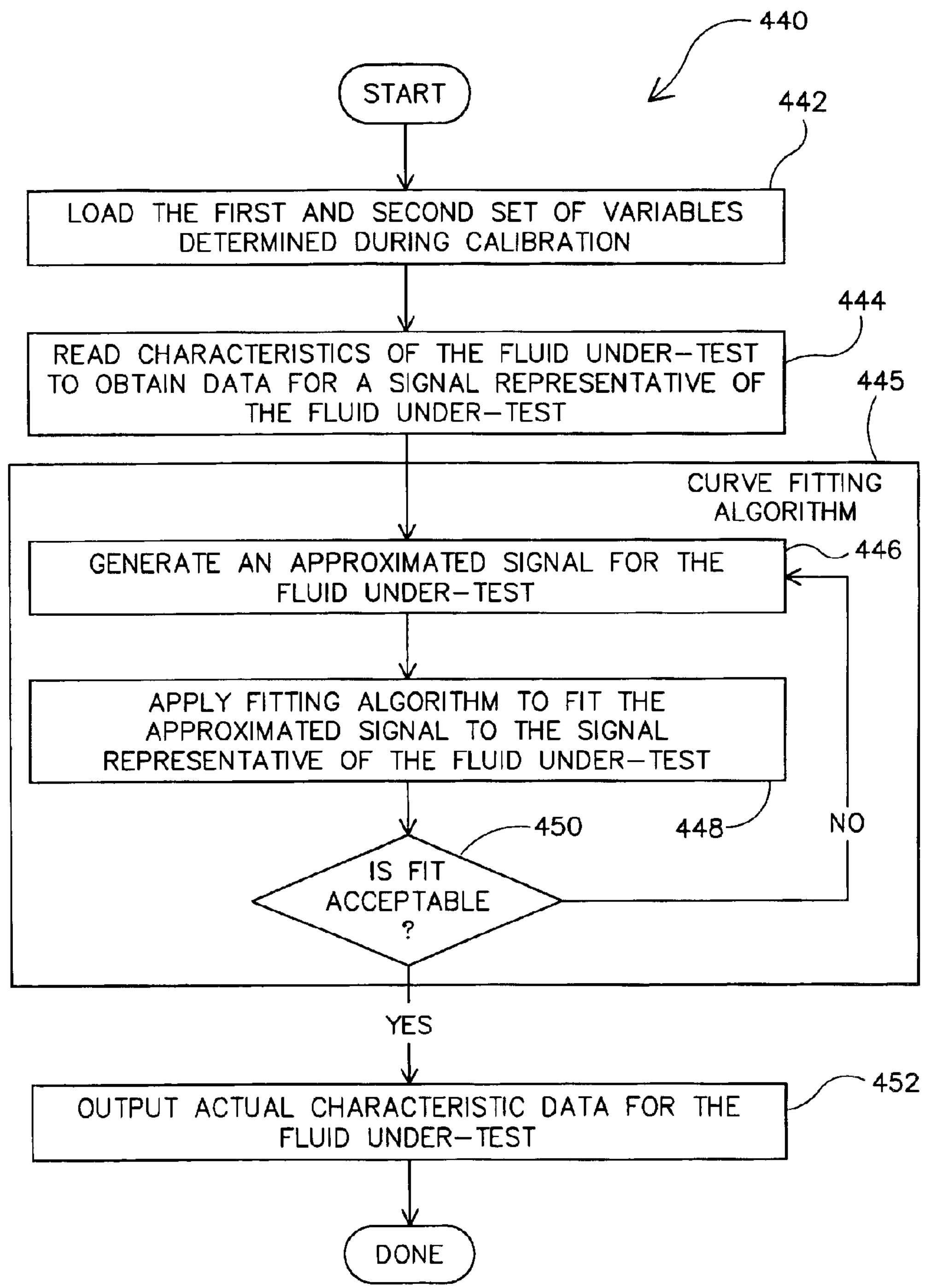
FIG. 10 is a flow chart diagram depicting method operations for executing a fitting algorithm, in accordance with one embodiment of the present invention.
Figure 11C:
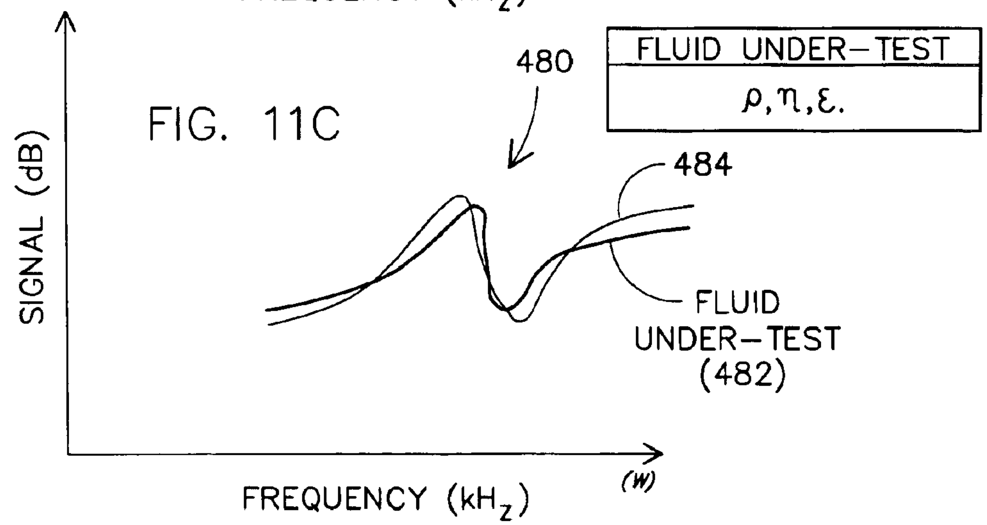

FIG. 10 illustrates a flowchart diagram 440 in which a curve fitting algorithm is performed in block 445, in accordance with one embodiment of the present invention. As mentioned above, the curve fitting algorithm is designed to fit approximated signal data for a particular fluid to an actual signal received from a fluid under-test as shown in FIG. 11C. The curve fitting algorithm is also applied to the process for obtaining the first calibration data and the second calibration data, in accordance with one embodiment.

The method begins at operation 442 where the first and second set of variables determined during calibration are loaded into memory. As mentioned above, the calibration data may be stored either on the ASIC itself in memory, or may be stored off the ASIC on a host computer or even on a removable storage media such as a magnetic card or the like. As mentioned above, the first and second set of variables determined to a calibration are most likely temperature dependent, and the calibration data will be identified for the particular temperature being sensed during the fluid under-test operation.

The method now moves to operation 444 where characteristics of the fluid under-test are read to obtain data for a signal representative of the fluid under-test. Reference is now made to FIGS. 2D and 2E where different oil types are provided with approximated fluid characteristics. For example, oil type 3 will include approximated fluid characteristics for density, viscosity, and the dielectric constant. Each of these approximated fluid characteristics along with the calibration variables, will be tied to a particular temperature. As the temperature rises, e.g., as shown in FIG. 2E, the values for the approximated fluid characteristics may also change, therefore defining slightly different values for the density viscosity and dielectric constant.

Once the data has been obtained from storage by way of a fetch, lookup or the like, these approximated fluid characteristic values are used to produce a signal representative of the fluid under-test. Reference is now made to FIG. 11C, where the signal that is representative of the fluid under-test is shown as signal 484. As can be seen, signal 484 is approximately similar to the signal provided by the actual fluid under-test, and shown as signal 482. In this example, the tuning fork has been inserted into the fluid under-test, and the frequency response of the tuning fork will produce the signal 482, as shown in FIG. 11C. Since the fluid under-test produced an actual signal 482, curve fitting the approximated signal that is representative of the fluid under-test, i.e., signal 484, will produce the actual fluid characteristic data for the fluid under-test signal 482. The result is that the fluid under-test fluid characteristic data, including the density, viscosity, and dielectric constant, will be generated for the actual fluid under-test.

Returning to FIG. 10, once the data is obtained for the signal that is representative of the fluid under-test, the method will move to operation 446. Operations 446, 448, and 450 will be part of a curve fitting algorithm defined in block 445. In operation 446, an approximated signal for the fluid under-test is generated. The approximated signal for the fluid under-test is shown in FIG. 11C as signal 484. The method will then move to operation 448 where a fitting algorithm is applied to fit the approximated signal to the actual signal for the fluid under-test. As mentioned above, this involves applying an algorithm that will merge the approximated signal 484 values onto the fluid under-test signal 482.

The curve fitting algorithm is a repetitive algorithm that will continuously operate until a suitable or best curve fitting result is produced. Thus, the method will move to decision operation 450, where it is determined whether the fit is acceptable. If the fit is not acceptable, meaning that the approximated signal 484 is not sufficiently close to the fluid under-test signal 482, the method will return to operation 446. In operation 446, the new updated approximated fluid characteristic variables are updated to the formula to then producing new approximated signal 484 that may be closer to the fluid under-test. Again, the method moves to operation 448 where the fitting algorithm is perform to again attempt to merge the approximated signal 484 onto the fluid under-test signal 482 as shown in FIG. 11C.

This method will continue until an acceptable curve fitting degree has been reached. If successive loops have occurred and the curve fitting does not improve, it is possible for the signal to be acceptable and the method will move to operation 452. In a preferred embodiment, the curve fitting algorithm will use a simplex equation curve fitting algorithm to assist in merging the approximated signal to the actual signal received from the fluid under-test. In a more preferred embodiment, the simplex equation will utilize operations to minimize the least squares values of a theoretical model. An example algorithm that may be used may include a downhill simplex algorithm for multidimensional applications. The algorithm is defined in a book entitled "The Art of Scientific Computing," having authors William H. et al. copyright date 1988. Specific pages of interest include, pages 305–309, chapter 10.4, entitled "Downhill Simplex Method in Multidimensions." This book is incorporated herein by references for all purposes. Of course, it should be understood that other fitting algorithms may also be used, so long as the function of "fitting" is achieved.

The method will then move to operation 452 where the actual determined characteristic data for the fluid under-test is output to produce the ascertained density, viscosity, and dielectric constant for the particular fluid under-test.

FIGS. 11A through 11B have been discussed above with reference to the curve fitting operations. Specifically, FIG. 11A illustrates a curve fitting operation that takes place in vacuum or air to obtain the first set of variables by curve fitting an approximated signal for vacuum or air 464 to an actual vacuum or air signal 462. FIG. 11B shows the curve fitting operation performed to merge an approximated signal 474 of a known fluid, to the actual response of the known fluid 472. By merging the approximated signal 474 to signal 472, which is the actual signal received from the known fluid, it is possible to obtain the second set of calibration variables A, B, and k. Finally, FIG. 11C illustrates the curve fitting operation that is performed during actual use of a tuning fork to obtain characteristic variables of a particular fluid under-test.

Figure 12:
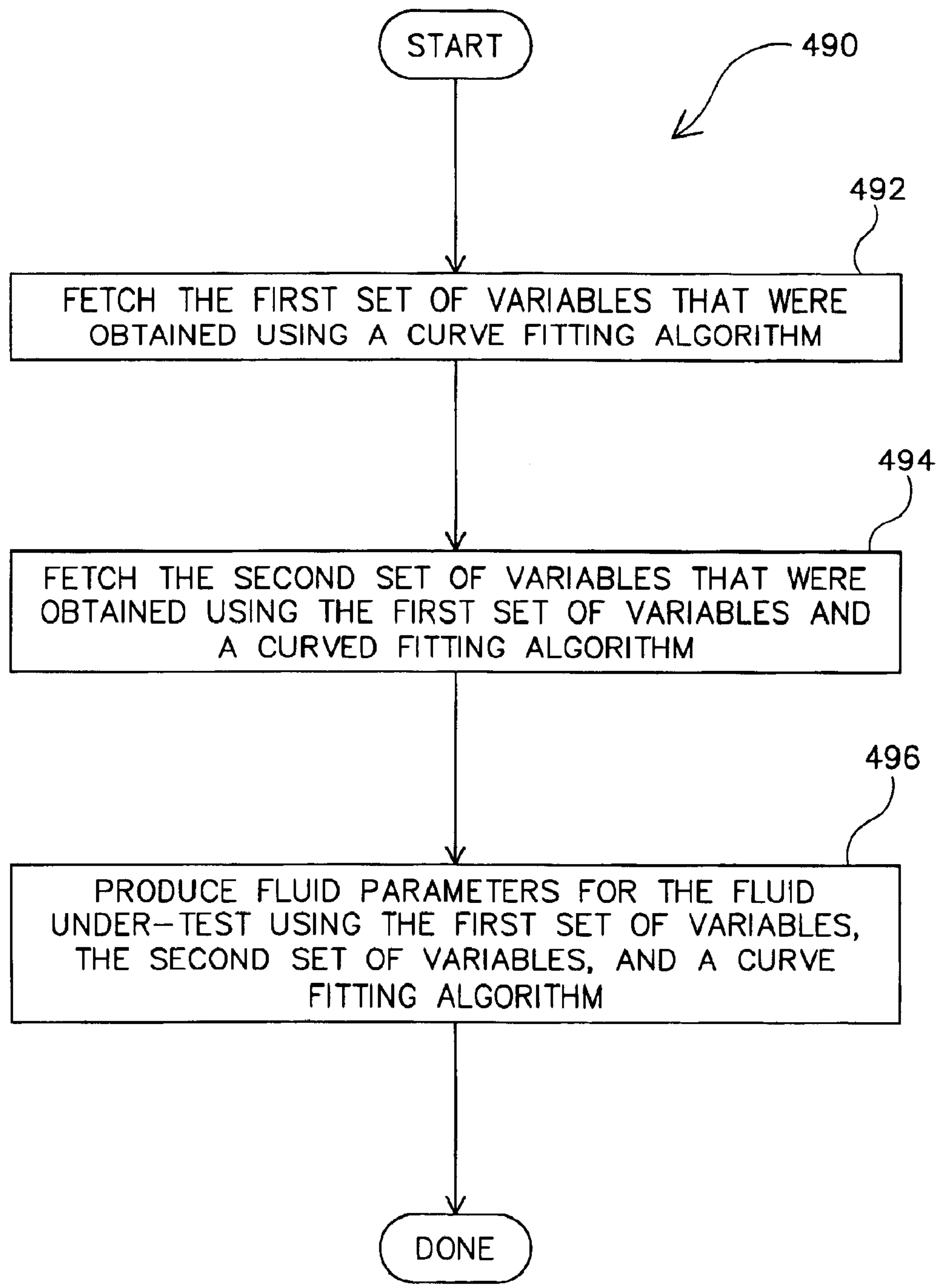
FIG. 12 illustrates a flow chart diagram depicting processing operations performed to determine characteristics of a fluid under-test, in accordance with one embodiment of the present invention.

FIG. 12 illustrates a flowchart diagram 490, depicting the basic functional process operations performed by an ASIC 118 to produce fluid parameters for a fluid under-test using a tuning fork, in accordance with one embodiment of the present invention. The method begins at operation 492 where the first set of variables that were obtained using a curve fitting algorithm are fetched from storage. The method then moves to operation 494 where the second set of variables that were obtained using the first set of variables and the curve fitting algorithm are also fetched from storage. As mentioned above, the second set of variables will define calibration variables for a particular tuning fork. The calibration variables will be stored either directly on the ASIC, off the ASIC, or on some storage medium. Once the calibration variables have been obtained, the processor that is either part of the ASIC or in communication with the ASIC, will produce fluid parameters for the fluid under-test using the first set of variables, the second set of variables, and the curve fitting algorithm in operation 496.

Examples of the tuning fork sensor of the present invention can be found in U.S. Provisional Patent Application No. 60/419,404, which is incorporated by reference herein. In summary, the tuning fork resonator is a mechanical piezoelectric resonator that is capable of measuring physical and electrical properties, such as the viscosity, density, dielectric constant, and the conductivity of a sample fluid.

The tuning fork resonator should be broadly construed to include any resonator that can oscillate in a fluid. Other example resonator structures may include tridents structures, cantilever structures, torsion bar structures, unimorph structures, bimorph structures, membrane resonator structures or combinations thereof.

In a most basic configuration, the sensing system of the present invention is configured with a sensor such as a mechanical resonator, a processor and a user interface to inform the user of a level and/or condition of the fluid. In this embodiment, the sensor receives an excitation signal from a signal generator, causing the sensor to resonate. The resonance of the sensor is proportionally related to the viscosity of the fluid, which is directly correlated to the type and present state of the fluid condition. The resulting resonance is transmitted via a generated output signal to a processor, which modifies the signal for analysis and compares it with a known value so as to determine the present state of the fluid.

Although the foregoing invention has been described in some detail for purposes of clarity of understanding, it will be apparent that certain changes and modifications may be practiced within the scope of the appended claims. For example, though a feature of an embodiment may described particularly in the context of engine oil, it is not to be limited to that application. The principles of the present invention have widespread application for other automotive vehicle fluids and in applications outside automotive applications (e.g., in devices for analyzing a property of a fluid flowing in a conduit in an oil field; in detectors associated with flow injection analysis instruments; in microbalances; in systems for high throughput research and screening; or otherwise). Accordingly, the present embodiments are to be considered as illustrative and not restrictive, and the invention is not to be limited to the details given herein, but may be modified within the scope and equivalents of the appended claims.

What is claimed is:

1. A system for sensing characteristics of a fluid, comprising:

a tuning fork configured to be at least partially submerged in a fluid under-test; and an application specific integrated circuit (ASIC), the ASIC including, analog input/output circuitry for providing stimulus to the tuning fork and receiving a response signal from the tuning fork;

conditioning circuitry for reducing analog signal offsets in the response signal;

signal detection circuitry for identifying amplitude data of the response signal;

analog-to-digital conversion circuitry for converting the detected amplitude data into digital form; and memory for holding user defined data, wherein the digital form of the response signal is processed in conjunction with the user defined data to generate fluid characteristics of the fluid under-test.

2. A system for sensing characteristics of a fluid as recited in claim 1, wherein the user defined data includes at least one of calibration data and approximated fluid characteristics of the fluid under-test.

3. A system for sensing characteristics of a fluid as recited in claim 2, further comprising:

a temperature sensor, the temperature sensor designed to read a temperature next to the tuning fork, the temperature reading being utilized to select a temperature specific set of calibration data and approximated fluid characteristics of the fluid under-test.

4. A system for sensing characteristics of a fluid as recited in claim 2, wherein one or both of the calibration data and approximated fluid characteristics of the fluid under-test are capable of being stored on one of a memory card, a memory stick, a hard drive, an optical disc, and on a network storage.

5. A system for sensing characteristics of a fluid as recited in claim 1, wherein the ASIC is in communication with a processor, the processor being configured to process a fitting algorithm to ascertain the fluid characteristics of the fluid under-test.

6. A system for sensing characteristics of a fluid as recited in claim 5, wherein the ASIC further includes an integrated CPU, the CPU being configured to process a fitting algorithm to ascertain the fluid characteristics of the fluid under-test.

7. A system for sensing characteristics of a fluid as recited in claim 6, wherein the fitting algorithm implements a simplex equation to minimize least squares values.

8. A system for sensing characteristics of a fluid as recited in claim 5, wherein the fitting algorithm implements a simplex equation to minimize least squares values.

9. A system for sensing characteristics of a fluid as recited in claim 1, wherein the ASIC is coupled to local machine electronics of a machine.

10. A system for sensing characteristics of a fluid as recited in claim 9, wherein the machine is an automobile and the fluid under-test is engine oil.

11. A system for sensing characteristics of a fluid as recited in claim 10, further comprising:

a local machine user interface for providing one of analog and digital data regarding the fluid characteristics of the fluid under-test.

12. A system for sensing characteristics of a fluid as recited in claim 9, wherein the local machine electronics includes engine control electronics.

13. A system for sensing characteristics of a fluid as recited in claim 1, wherein the ASIC includes digital logic control for interfacing components internal to the ASIC to components external to the ASIC.

14. A system for sensing characteristics of a fluid as recited in claim 13, wherein the ASIC is integrated into electronics of one of a motor, a measurement while drilling tool, a logging while drilling tool, an exploration and production well logging tool, a printed circuit board, and a computer motherboard.

15. A system for sensing characteristics of a fluid as recited in claim 1, wherein the generated generate fluid characteristics of the fluid under-test are displayed on a display monitor.

16. A system for sensing characteristics of a fluid as recited in claim 1, wherein the memory is rewritable.

17. A system for sensing characteristics of a fluid as recited in claim 1, wherein the ASIC further comprises:

glue logic for interfacing components of the ASIC.

18. A system for sensing characteristics of a fluid as recited in claim 1, wherein the ASIC further comprises:

a digital I/O for interfacing with a computer.

19. A system for sensing characteristics of a fluid as recited in claim 1, wherein the ASIC further comprises:

a ROM;

a RAM;

a CPU; and a clock.

20. A system for sensing characteristics of a fluid as recited in claim 1, wherein the ASIC further comprises:

a timer.

21. A system for sensing characteristics of a fluid as recited in claim 1, wherein the tuning fork has an integrated capacitor.

22. A system for sensing characteristics of a fluid as recited in claim 21, wherein the capacitor is integrated on the tuning fork.

23. A system for sensing characteristics of a fluid as recited in claim 22, further including, a capacitor coupled to an input of the differential amplifier.

24. A system for sensing characteristics of a fluid as recited in claim 1, wherein the signal conditioning circuitry includes, a differential amplifier for receiving an input from tuning fork, the input from the tuning fork being the response signal; and a capacitor coupled to an input of the differential amplifier.

25. A system for sensing characteristics of a fluid as recited in claim 1, wherein the signal conditioning circuitry includes, a differential amplifier for receiving an input from tuning fork, the input from the tuning fork being the response signal; and a digital-to-analog converter for providing compensation to one of the signal detection circuitry and the analog-to-digital converter.

26. A system for sensing characteristics of a fluid as recited in claim 1, wherein the signal conditioning circuitry includes, a differential amplifier for receiving an input from tuning fork, the input from the tuning fork being the response signal;

a capacitor coupled to an input of the differential amplifier; and a summation amplifier, the summation amplifier coupled between the differential amplifier and the capacitor.

27. A circuit for determining characteristics of a fluid under-test, comprising:

analog-to-digital processing circuitry for interfacing with a sensor and host electronics, the analog-to-digital processing circuitry including, a frequency generator for providing stimulus to the sensor;

conditioning circuitry for receiving a response signal from the sensor and reducing analog signal offsets in the response signal;

signal detection circuitry for identifying amplitude data of the response signal;

analog-to-digital conversion circuitry for converting the detected amplitude data into digital form; and memory capable of holding data characterizing the sensor, wherein the digital form of the response signal is processed to generate fluid characteristics of the fluid under-test.

28. A circuit for determining characteristics of a fluid under-test as recited in claim 27, wherein the data characterizing the sensor includes calibration data.

29. A circuit for determining characteristics of a fluid under-test as recited in claim 27, wherein the memory further being capable of holding approximated characteristic data of the fluid under-test.

30. A system for determining characteristics of a fluid as recited in claim 27, wherein the analog-to-digital processing circuitry is incorporated into an application specific integrated circuit (ASIC).

31. A system for determining characteristics of a fluid as recited in claim 27, wherein the signal conditioning circuitry and the memory are integrated into an application specific integrated circuit (ASIC).

32. A system for determining characteristics of a fluid as recited in claim 27, wherein the signal conditioning circuitry, the signal detection circuitry, and the memory are integrated into an application specific integrated circuit (ASIC).

33. A system for determining characteristics of a fluid as recited in claim 27, wherein the signal conditioning circuitry, the signal detection circuitry, the frequency generator, and the memory are integrated into an application specific integrated circuit (ASIC).

34. A system for determining characteristics of a fluid as recited in claim 27, wherein the signal conditioning circuitry, the signal detection circuitry, the frequency generator, the analog-to-digital conversion circuitry and the memory are integrated into an application specific integrated circuit (ASIC).

35. A system for determining characteristics of a fluid as recited in claim 34, wherein the ASIC further includes an integrated processor.

36. A system for determining characteristics of a fluid as recited in claim 35, wherein the integrated processor is one of a CPU, a microprocessor core, a microcontroller, a state machine, a digital signal processor.

37. A system for determining characteristics of a fluid as recited in claim 27, wherein the signal detection circuitry includes one of an RMS detector and a synchronous detector.

38. A system for determining characteristics of a fluid as recited in claim 27, wherein the sensor is a mechanical resonator.

39. A system for determining characteristics of a fluid as recited in claim 38, wherein the mechanical resonator is a tuning fork.

40. A system for determining characteristics of a fluid as recited in claim 27, wherein the sensor is a tuning fork with an integrated capacitor.

41. A system for determining characteristics of a fluid as recited in claim 28, wherein the ASIC is integrated with the sensor.

42. A system for determining characteristics of a fluid as recited in claim 28, wherein the ASIC is integrated in vehicle electronics.

43. A system for determining characteristics of a fluid as recited in claim 28, wherein the fluid under-test is vehicle fluid.

44. A system for determining characteristics of a fluid as recited in claim 28, wherein the vehicle fluid is oil.

45. A method for interfacing with a mechanical sensor to obtain characteristics of a fluid under-test, the mechanical sensor being at least partially submerged in the fluid under-test, the method comprising:

applying a variable frequency signal to the sensor;

receiving a frequency response from the sensor;

conditioning the frequency response;

detecting signal components of the frequency response;

converting the frequency response to digital form, the digital form being representative of the frequency response received from the sensor;

fetching first calibration variables from memory, the first calibration variables defining physical characteristics of the sensor;

fetching second calibration variables from memory, the second calibration variables defining characteristics of the sensor in a known fluid; and processing the digital form of the response received from the sensor when in the fluid under-test along with the fetched first and second calibration variables, the processing implementing a fitting algorithm to produce fluid characteristics of the fluid under-test.

46. A method for interfacing with a mechanical sensor to obtain characteristics of a fluid under-test as recited in claim 45, wherein the fluid characteristics produced for the fluid under-test include density, viscosity and dielectric constant values.

47. A method for interfacing with a mechanical sensor to obtain characteristics of a fluid under-test as recited in claim 45, wherein the fitting algorithm executes a simplex equation to minimize least squares.

48. A method for interfacing with a mechanical sensor to obtain characteristics of a fluid under-test as recited in claim 45, wherein the first calibration of the sensor is performed in one of air and vacuum.

49. A method for interfacing with a mechanical sensor to obtain characteristics of a fluid under-test as recited in claim 45, wherein known fluid is a volatile fluid.

50. A method for interfacing with a mechanical sensor to obtain characteristics of a fluid under-test as recited in claim

45, wherein the first calibration and the second calibration utilize the fitting algorithm.

51. A method for interfacing with a mechanical sensor to obtain characteristics of a fluid under-test as recited in claim 45, wherein the method operations are executed using circuitry.

52. A method for interfacing with a mechanical sensor to obtain characteristics of a fluid under-test as recited in claim 45, wherein some of the circuitry is part of an application specific integrated circuit (ASIC).

* * * * *